US009771533B2

(12) United States Patent
Lilga et al.

(10) Patent No.: US 9,771,533 B2
(45) Date of Patent: *Sep. 26, 2017

(54) SYSTEMS AND PROCESSES FOR CONVERSION OF ETHYLENE FEEDSTOCKS TO HYDROCARBON FUELS

(71) Applicant: BATTELLE MEMORIAL INSTITUTE, Richland, WA (US)

(72) Inventors: Michael A. Lilga, Richland, WA (US); Richard T. Hallen, Richland, WA (US); Karl O. Albrecht, Richland, WA (US); Alan R. Cooper, Richland, WA (US); John G. Frye, Richland, WA (US); Karthikeyan Kallupalayam Ramasamy, West Richland, WA (US)

(73) Assignee: Battelle Memorial Institute, Richland, WA (US)

( * ) Notice: Subject to any disclaimer, the term of this patent is extended or adjusted under 35 U.S.C. 154(b) by 100 days.

This patent is subject to a terminal disclaimer.

(21) Appl. No.: 14/528,185

(22) Filed: Oct. 30, 2014

(65) Prior Publication Data

US 2016/0194572 A1 Jul. 7, 2016

(51) Int. Cl.
| | |
|---|---|
| *C07C 2/12* | (2006.01) |
| *C10L 1/04* | (2006.01) |
| *C10G 29/20* | (2006.01) |
| *C10G 45/00* | (2006.01) |
| *C10G 50/00* | (2006.01) |
| *C10G 69/12* | (2006.01) |
| *C10G 3/00* | (2006.01) |
| *C07C 2/24* | (2006.01) |
| *C07C 2/66* | (2006.01) |
| *C07C 5/03* | (2006.01) |

(52) U.S. Cl.
CPC ...... *C10L 1/04* (2013.01); *C07C 2/12* (2013.01); *C07C 2/24* (2013.01); *C07C 2/66* (2013.01); *C07C 5/03* (2013.01); *C10G 3/00* (2013.01); *C10G 29/205* (2013.01); *C10G 45/00* (2013.01); *C10G 50/00* (2013.01); *C10G 69/123* (2013.01); *C10G 69/126* (2013.01); *C07C 2521/04* (2013.01); *C07C 2521/12* (2013.01); *C07C 2523/42* (2013.01); *C07C 2523/755* (2013.01); *C07C 2529/06* (2013.01); *C07C 2529/40* (2013.01); *C07C 2529/70* (2013.01); *C07C 2529/76* (2013.01); *C10G 2300/1081* (2013.01); *C10G 2300/1092* (2013.01); *C10G 2300/1096* (2013.01); *C10L 2200/0469* (2013.01); *C10L 2270/02* (2013.01); *C10L 2270/04* (2013.01); *C10L 2290/24* (2013.01); *C10L 2290/543* (2013.01); *Y02P 30/42* (2015.11)

(58) Field of Classification Search
CPC ......... C07C 2/06; C07C 2/02; C07C 2521/04; C07C 2521/12; C07C 2523/42; C07C 2523/755; C07C 2529/06; C07C 2529/40; C07C 2529/70; C07C 2529/76; C07C 2/12; C07C 2/24; C07C 2/66; C07C 5/03; C10G 2300/1081; C10G 2300/1092; C10G 2300/1096; C10G 29/205; C10G 3/00; C10G 45/00; C10G 50/00; C10G 69/123; C10G 69/126
USPC .......... 585/329, 330, 517, 523, 527
See application file for complete search history.

(56) References Cited

U.S. PATENT DOCUMENTS

| | | | |
|---|---|---|---|
| 8,378,160 B2 * | 2/2013 | Gruber .......... | C07C 1/24 585/240 |
| 8,957,270 B2 | 2/2015 | Berard et al. | |
| 2011/0124938 A1 | 5/2011 | Inoue et al. | |
| 2012/0197053 A1 | 8/2012 | Cantrell et al. | |
| 2014/0114101 A1 | 4/2014 | Greene et al. | |
| 2015/0094506 A1 * | 4/2015 | Fichtl .......... | C10G 3/50 585/310 |

FOREIGN PATENT DOCUMENTS

| | | |
|---|---|---|
| WO | 2014008337 A1 | 1/2014 |
| WO | 2014154799 A1 | 10/2014 |

OTHER PUBLICATIONS

International Search Report/Written Opinion for International Application No. PCT/GB2015/053243, International Filing date Oct. 29, 2015.
International Search Report/Written Opinion for International Application No. PCT/GB2015/053242, International Filing Date Oct. 29, 2015.
Espinoza, R. L., et al., Catalytic oligomerization of ethene over nickel-exchanged amorphous silica-aluminas; effect of the acid strength of the support, Applied Catalysis, 29, 2013, 1987, 295-303.
Heveling, J., et al., Catalysts and conditions for the highly efficient, selective and stable heterogeneous oligomerization of ethylene, Applied Catalysis, 173, 2013, 1-9.
Hulea, V., et al., Ni-exchanged A1MCM-41—An efficient bifunctional catalyst for ethylene oligomerization, Journal of Catalysis, 1, 2004, 213-222.
Yamamura, M., et al., Synthesis of ZSM-5 zeolite with small crystal size and its catalytic performance for ethylene oligomerization, Zeolites, 14, 1994, 643-649.

* cited by examiner

*Primary Examiner* — Sharon Pregler
(74) *Attorney, Agent, or Firm* — Klarquist Sparkman, LLP

(57) ABSTRACT

Systems, processes, and catalysts are disclosed for obtaining fuels and fuel blends containing selected ratios of open-chain and closed-chain fuel-range hydrocarbons suitable for production of alternate fuels including gasolines, jet fuels, and diesel fuels. Fuel-range hydrocarbons may be derived from ethylene-containing feedstocks and ethanol-containing feedstocks.

45 Claims, 14 Drawing Sheets

SYSTEMS AND PROCESSES FOR CONVERSION OF ETHYLENE FEEDSTOCKS TO HYDROCARBON FUELS

STATEMENT REGARDING RIGHTS TO INVENTION MADE UNDER FEDERALLY-SPONSORED RESEARCH AND DEVELOPMENT

This invention was made with Government support under Contract DE-AC05-76RL01830 awarded by the U.S. Department of Energy. The Government has certain rights in the invention.

FIELD OF THE INVENTION

The present invention relates generally to processes and catalysts for conversion of hydrocarbon feedstocks. More particularly, the invention relates to a system, processes, and catalysts for conversion of ethylene-containing feedstocks to fuel-range hydrocarbon distillates suitable for production of fuels.

BACKGROUND OF THE INVENTION

Currently a need exists for alternative hydrocarbon fuels, especially aviation and diesel fuels, from domestic sources to enhance energy security and to decrease reliance on foreign petroleum. Current routes to alternative fuels are limited by strict fuel standards and limited fuel feed stocks. And, many fuel and fuel blend stocks require open-chain hydrocarbons including, e.g., normal paraffins and branched paraffins. For example, according to ASTM D7566-11a standards, hydrogenated HEFA/SPK (Hydroprocessed Esters and Fatty Acids/Synthetic Paraffinic Kerosene) from bio-derived fats and oils and from Fischer-Tropsch reactions of syngas can only contain a maximum of 0.5% aromatics and 15% cycloparaffins. In addition, an average JP-8 jet fuel contains 59% normal and iso-paraffins, the remainder being aromatics and cycloparaffins. However, many conventional methods for producing alternate fuels such as from biomass feedstocks cannot meet these requirements. For example, pyrolysis and hydrothermal liquefaction of terrestrial biomass feedstocks form aromatics predominately and, when hydrotreated, yield cyclic hydrocarbons. Ethanol and other oxygenated hydrocarbons are suitable for direct blending with gasoline, but oxygenated hydrocarbons are precluded for use in jet fuels. Ethanol can be converted to liquid hydrocarbons over solid acid catalysts only at temperatures above about 300° C., but the products are largely aromatics (75%-90%). Thus, aviation and military organizations can expect difficulties meeting renewable fuel standards for jet fuels and diesel fuels using conventional technologies. Yet, ethanol is available in the market place. Thus, converting ethanol to oxygen-free open-chain hydrocarbons could permit their use in diesel and jet fuels. More specifically, catalytic conversion of renewable ethanol to oxygen-free open-chain hydrocarbons could allow for production of renewable fuels from oxygenated renewable feedstocks, such as carbohydrates and lignocellulosic biomass.

Ethylene is a feedstock available from numerous sources that could be converted to alternate open-chain hydrocarbon fuels. Ethylene can be obtained from sources such as natural gas, coal, and petroleum. Ethylene is also obtainable by known technologies from ethanol, which in turn can be made from biomass-derived sugars and starch and from syngas. Ethanol therefore can be considered an ethylene precursor. However, conversion of ethylene via conventional direct, single step conversion processes catalyzed by solid acid catalysts, such as silicoaluminates, is typically characterized by high process temperatures (>280° C.) that form large quantities of coke, and extensive formation of aromatic compounds up to 70 wt %. Single-step processes such as that reported by Heveling et al. over Ni/Si—Al and other catalysts are reported to produce open-chain hydrocarbons at high ethylene conversions, but with selectivities to $\geq$C10 of only ca 40% and to $\geq$C8 of only about 63%. Further, multi-step conversion processes reported in the literature have potentially better selectivities to open-chain compounds, but conversions to date are low and significant quantities of aromatic compounds are produced. For example, Synfuels International reports a multi-step process using Ni catalysts at process temperatures from 220° C. to 240° C. that produces a product composition containing between 4% to 90% aromatics. At the reported maximum selectivity of 70% middle distillate products and an ethylene conversion of only 26%, the maximum possible product yield in the middle distillate range is only about 18%. The 2-step Synfuels International process does not improve upon and, in fact, gives a lower distillate yield (18%) than the 1-step process reported by Heveling (40%). Thus, the 2-step approach by Synfuels International does not represent an economically feasible approach for obtaining high yields of distillate fuels. Accordingly, new processes and catalysts are needed that convert ethylene obtained, e.g., from various ethanol feedstocks into suitable oxygen-free hydrocarbon fuel blend stocks that minimize the production of aromatic hydrocarbons and the quantity of hydrogen needed to produce fuels, and that produce fuel precursors and/or fuel blend stocks that maximize flexibility in blending ratios suitable for production of jet fuel, other aviation fuels, diesel, and heating fuels. The present invention addresses these needs using, surprisingly, a 2-step method that provides distillate yields greater than the 18% of the prior art.

Definitions

The following terms are defined herein for purposes of this application.

Fuel-Range Hydrocarbons: are defined as any oxygen-free hydrocarbon or hydrocarbon mixture with a carbon number ranging between about C8 and about C23 that distills in a temperature range from about 120° C. to about 390° C. Actual range limits for commercial use depend on numerous other required fuel properties. Thus, no limitations are intended. Fuel-range hydrocarbons can be fractionated to produce jet, diesel, other aviation fuels and fuel blend stocks suitable for commercial and military applications, and heating fuels.

Jet Fuel and Jet-Range Hydrocarbons: are defined as any hydrocarbon or hydrocarbon mixture that distills in the range from about 120° C. to about 300° C., and typically includes hydrocarbons with a carbon number between about 08 and about 016. Actual range limits for commercial use depend on numerous other required fuel properties. Thus, no limitations are intended.

Diesel Fuel and Diesel-Range Hydrocarbons: are defined as any hydrocarbon or hydrocarbon mixture that distills in the range of about 160° C. to about 390° C., typically with a carbon number between about C11 and about C23. Actual range limits for commercial use depend on numerous other required fuel properties. Thus, no limitations are intended.

Alternative Fuel—The term "alternative" refers to hydrocarbons derived from non-petroleum sources, including renewable sources such as, e.g., biomass, sugars, starches, lignocellulose, and other renewable sources, and other sources such as natural gas and coal.

Boiling Point Cut-Off: is a temperature defining the high or low temperature of a boiling point range. The degree to which materials are present that actually boil outside the defined range depends on the efficiency of the distillation apparatus and operating conditions so that the cut-off points are to be considered approximate and are not absolute. Boiling point cut-offs are determined herein by research and process chemistry needs and not necessarily by current industry standards. Boiling point cut-offs that produce fuel fractions that meet industrial standards from disclosed products are easily determined by those of ordinary skill in the art using established testing and research methods and may differ from those defined here. Alternate terms are distillation cut-off point and fractionation temperature.

Light Products: are defined as any hydrocarbon or hydrocarbon mixture that boils below a distillation cut-off point. An alternate term is light fraction.

Heavy Products: are defined as any hydrocarbon or hydrocarbon mixture that boils above a distillation cut-off point. An alternate term is heavy fraction Two-Step or Two-Stage—A two-step process or two-stage system described herein employs two sequential olefin oligomerization process steps or system stages to produce fuel-range hydrocarbons. Other required and optional process steps or system stages may be used to obtain desired hydrocarbon fuels or fuel blend stocks with desired properties.

One-Step or One-Stage—A one-step process or one-stage system employs a single ethanol oligomerization step or stage to produce fuel-range hydrocarbons. Other required and optional process steps or system stages may be used to obtain desired hydrocarbon fuels or fuel blend stocks with desired properties.

Olefin—The term "olefin" or alternately, alkene, refers to any unsaturated hydrocarbon containing at least one double bond positioned along the length of the hydrocarbon chain. The hydrocarbon chain may be straight (i.e., acyclic, linear, or normal), cyclic, or branched (e.g., containing one or more hydrocarbon side-chains).

Weight Hourly Space Velocity (WHSV)—feedstock flow rate in grams/hour divided by the catalyst weight in grams.

SUMMARY OF THE INVENTION

The present invention includes a two-step oligomerization process and two-stage oligomerization system for controlled catalytic conversion of ethylene-containing feedstocks that produce fuel-range hydrocarbon distillates containing primarily open-chain oligomers including, e.g., normal paraffins and isoparaffins. The present invention achieves results that conventional conversion processes cannot. For example, the present invention converts ethylene (or ethanol as a precursor to ethylene) to distillate normal and isoparaffins with high ethylene conversion (e.g., 50% to 100%), high product selectivities in the distillate range (e.g., 75 wt %≥C8 and 55 wt %≥C10) in a single-pass operation (higher with recycle), and <4 wt % aromatic compounds prior to hydrotreating. Unreacted materials are easily recycled to increase fuel yields. As such, the present invention addresses the need for low aromatic alternate fuels and fuel blend stocks.

The invention also includes a two-step process combined with a one-step process and system for controlled catalytic conversion of ethylene-containing feedstocks (or ethanol as a precursor to ethylene) and ethanol-containing feedstocks to produce fuel-range hydrocarbon distillates containing open-chain oligomers including, e.g., normal paraffins and isoparaffins, and closed-chain oligomers including, e.g., cyclic paraffins and aromatic hydrocarbons in any desired concentration. The combined process and system make a low aromatic fuel blend stock as described above. The combined process employs a parallel one-step process or one-stage system to produce an aromatic fuel blend stock. For example, ethanol can be converted in a one-step method over zeolyte catalysts to mostly aromatic hydrocarbons. In one application, the aromatics may be alkylated with olefin products obtained from a first oligomerization reactor of a two-step process or two-stage system; with light olefin products fractionated from the second oligomerization reactor of the two-step process or two-stage system; or with ethylene to form higher molecular weight aromatic products in the distillate range.

In another application, the aromatic hydrocarbons can be reduced with a catalyst and hydrogen to prepare cyclic hydrocarbons. Thus, in the combined process or combined system, one-step or one-stage products comprising a fuel blend stock containing cyclic paraffins and aromatics can be blended or mixed in any desired ratio with two-step or two-stage products comprising a fuel blend stock containing normal and isoparaffins to produce a fuel mixture containing all fuel components of any desired composition The two-step oligomerization process may include a first oligomerization step in which ethylene in an ethylene-containing feedstock from any source may be converted over a first catalyst at a temperature between about 40° C. and about 220° C. into oligomers that form a first oligomerization product containing a majority of low-molecular weight olefins with a carbon number between about C4 and about C8. Ethylene in the ethylene-containing feedstock may be derived from various sources including, but not limited to, e.g., biomass, cellulose, lignocellulose, starch, natural gas, coal, and petroleum, and methanol- and ethanol-containing streams, including combinations of these various sources. In some applications, low-molecular weight olefins derived from ethylene may include mixtures comprising even carbon number olefins, predominately butenes, hexenes, and octenes, such as 70% C4, 27% C6, and 3% C8. In other applications, the ethylene-containing feedstock may also contain propylene, such as when the ethylene-containing feed is derived from methanol, and the low-molecular weight olefin mixture will additionally contain odd-carbon olefins, such as C5, C7, and C9.

A second oligomerization step may convert the first oligomerization product over a second catalyst at a temperature between about 150° C. and about 350° C. to form a second oligomerization product containing a mixture of branched open-chain olefins, a selected fraction of which comprise fuel-range hydrocarbons and a second fraction comprising second oligomerization light products boiling below a distillation cut-off point. In some embodiments, the second oligomerization product prior to any optional post-processing operations contains between about 0% and about 4% aromatics by weight.

In some applications, the first oligomerization product may be further subjected to one or more processes such as oligomerization or fractionation to obtain olefin products or feedstocks of interest. For example, 2-butenes in the first oligomerization product may undergo olefin metathesis with ethylene by known technology to form propene. Propene is a valuable product that may be used for any of a number of known industrial processes, such as the production of acrylic acid or acrylonitrile. Propene may also be returned to the second oligomerization reactor for fuel production. The first oligomerization product may also be used in a separate process step as a feedstock for alkylation of aromatic compounds. For example, in some applications, aromatic hydrocarbons produced from the one-step catalytic conversion of ethanol can be alkylated to form higher molecular weight hydrocarbons, increasing carbon yield in the jet fuel range.

Likewise, in some applications, the second oligomerization product may be further subjected to one or more optional post-processing operations such as fractionation, recycling, aromatization, alkylation, olefin metathesis, hydrotreatment, and/or other processes to obtain distillates or fractions containing selected fuel-range hydrocarbons of interest. For example, in some applications the olefinic light products from fractionation of the second oligomerization can be recycled to the second oligomerization reactor inlet for further conversion to fuel-range hydrocarbons. In some applications, the olefinic light products from the second oligomerization can be sent to a reactor for conversion to aromatics. In some applications, these aromatics or aromatic hydrocarbons produced from one-step catalytic conversion of ethanol can also be alkylated with olefinic light products from the second oligomerization. In some applications, products from the second oligomerization may be fractionated, then hydrotreated to form a fuel-range hydrocarbons. In some applications, products from the second oligomerization may be hydrotreated, then fractionated to form fuel-range hydrocarbons.

Hydrotreated distillates from the two-step process may contain various classes of hydrocarbons of various molecular masses including, but not limited to, e.g., paraffins, cycloparaffins, aromatics, and/or other hydrocarbons. Hydrotreated distillates of the present invention containing fuel-range hydrocarbons may be blended and/or combined in various ways to produce various renewable hydrocarbon fuels including, but not limited to, e.g., aviation fuels, jet fuels, diesel fuels, gasoline, and/or other hydrocarbon fuels of interest.

The 2-stage system may include a first reactor or reactor stage containing a metal catalyst comprising nickel (Ni) supported on a crystalline or amorphous solid aluminosilicate support. The reactor may be pressurized with a feed gas comprising ethylene that optionally contains an inert gas such as nitrogen at total pressures selected in the range from 0 psig to 1200 psig. The first stage reactor may include a feed gas purification system to remove traces of oxygen and water. The first stage reactor may yield a first oligomerization product that contains olefins (alkenes) that correspond to successive combinations of ethylene, such as butenes, hexenes, octenes and small amounts of higher olefins with even carbon numbers.

The system may also include a second reactor or second reactor stage that may be optionally pressurized with a gas such as nitrogen and that contains an acid catalyst. The acid catalyst may convert olefins in the first oligomerization product from the first reactor stage to form a second oligomerization product containing fuel-range hydrocarbons. The fuel-range hydrocarbons may contain larger-chain oligomers with a carbon number from about C8 to about C23. Fuel-range hydrocarbons in the second oligomerization product may include, but are not limited to, e.g., normal and branched olefins and, depending upon conditions, low concentrations of aromatics.

The present invention also includes a process for one-step conversion of ethanol-containing feedstocks to aromatics and other hydrocarbon products described herein that can be directly hydrogenated to form cyclic hydrocarbons and/or can be alkylated to obtain higher molecular weight hydrocarbons suitable for production of jet and diesel fuels. For example, in some applications, zeolite catalysts may be used to convert ethanol to form a "clean" aromatic product containing no appreciable quantity of undesirable durene (1,2,4,5-tetramethylbenzene). Aromatics may be alkylated to form higher molecular weight hydrocarbons or may be hydrogenated (reduced) to produce oxygen-free cyclic hydrocarbons suitable for use in production of desired hydrocarbon fuels.

The present invention also includes a one-stage oligomerization system for catalytic conversion of ethanol-containing feedstocks that produce olefins (alkenes) and aromatics. Ethanol conversion over zeolite catalysts, such as HZSM-5, primarily forms diethyl ether through intermolecular dehydration at temperatures between 175° C. and 250° C. At higher temperatures, for example at about 280° C., intramolecular dehydration forms ethylene. Above about this temperature, ethanol forms ethylene and the ethylene undergoes a number of reactions (e.g., oligomerization, dehydrocyclization, hydrogenation, and cracking) to form a complex mixture of hydrocarbon products (i.e., paraffins, olefins, saturated cyclics, aromatics, and naphthalene), typically with a carbon number between C2 and C12 and with a product distribution that depends upon the processing temperature.

The present invention also includes a combined two-step and one-step oligomerization process and a combined two-stage and one-stage oligomerization system for catalytic conversion of ethylene-containing feedstocks and ethylene precursor ethanol-containing feedstocks that can be hydrotreated to produce normal paraffins, iso-paraffins cycloparaffins, indans, tetralins, and alkylated aromatics that may be blended to produce various alternative fuel blend stocks suitable for formation of various hydrocarbon fuels including, e.g., gasolines, jet fuel, and diesel fuel. The combined process and system use the individual two-step and one-step processes or two-stage and one-stage systems described above to make blend stocks that can be mixed or blended to make fuels of any desired composition. Thus, in some applications, combining hydrocarbon products obtained from the two-step process or the two-stage system with products from the one-step process or one-stage system can provide all required compounds necessary to produce a 100% alternative fuel. Composition of the fuel is determined by the quantities of each blend stock mixed together.

The purpose of the foregoing abstract is to enable the United States Patent and Trademark Office and the public generally, especially scientists, engineers, and practitioners in the art who are not familiar with patent or legal terms or phraseology, to determine the nature and essence of the technical disclosure of the application. The abstract is neither intended to define the invention of the application, which is measured by the claims, nor is it intended to be limiting as to the scope of the invention in any way.

DETAILED DESCRIPTION

Systems and processes are detailed for catalytic conversion of ethylene-containing and/or ethylene precursor ethanol-containing feedstocks into fuel-range distillates and fuel-blending feedstocks for production of alternative (including renewable) fuels. In the following description, embodiments of the present invention are shown and described by way of illustration of the best mode contemplated for carrying out the invention. It will be clear that the invention may include various modifications and alternative constructions. Accordingly, the description of the preferred embodiments should be seen as illustrative only and not limiting. The present invention includes all modifications, alternative constructions, and equivalents falling within the spirit and scope of the invention as defined in the claims. A controlled 2-step/2-stage oligomerization will now be described that produces primarily normal and isoparaffin hydrocarbons, forms minimal aromatics, has high carbon efficiency in the distillate range (especially for jet and diesel fuels), minimizes formation of naptha-like components, and allows efficient intermediate product recycling as one means to increase product yield in the distillate range.

Two-Step Oligomerization Process

Figure 1:
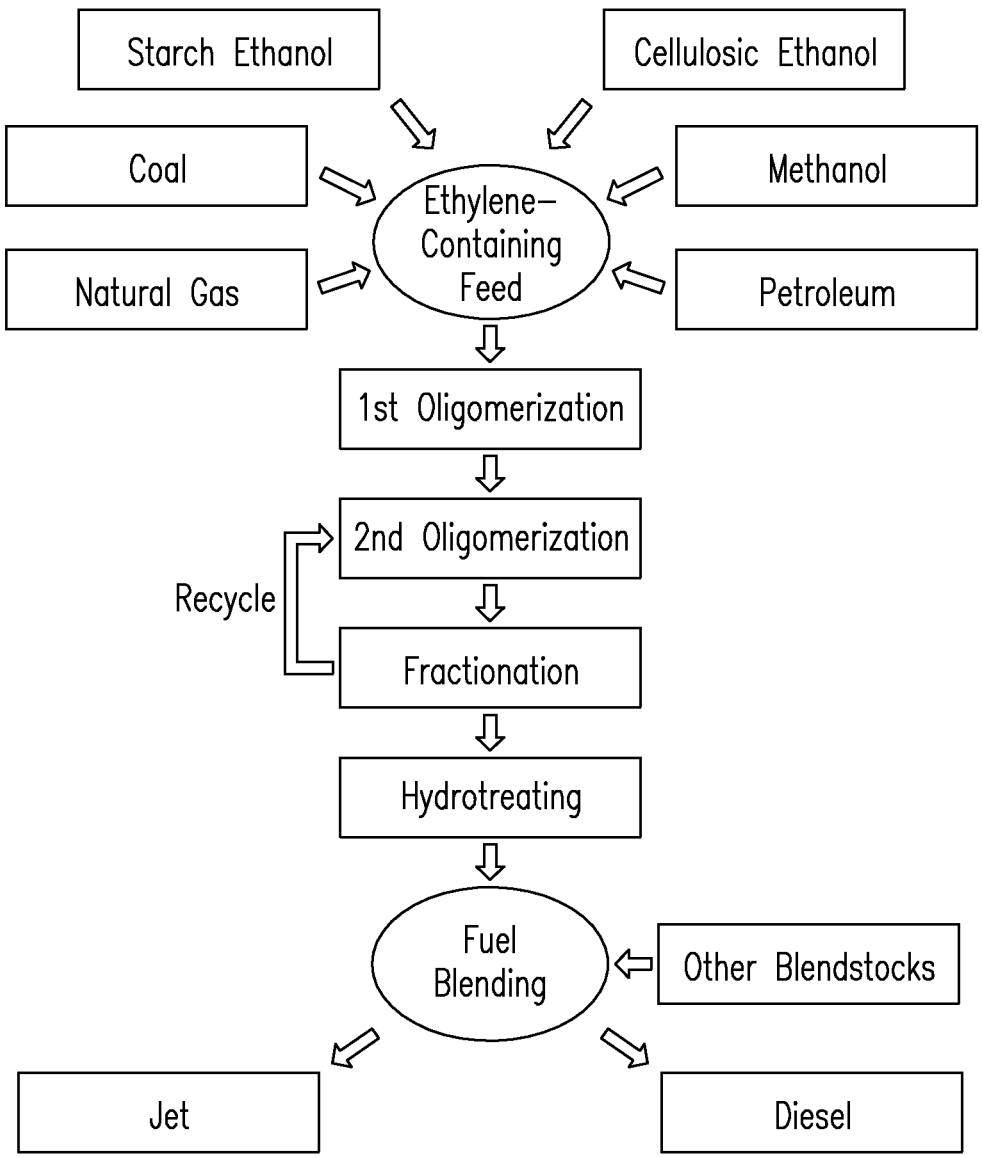
FIG. 1 shows an exemplary two-step process for conversion of an ethylene-containing feedstock into fuel-range hydrocarbons suitable for production of alternative (including renewable) hydrocarbon fuels, according to one embodiment of the process of the present invention.

FIG. 1 shows an exemplary two-step oligomerization process for catalytic conversion of ethylene-containing feedstocks that, in the preferred mode of operation, yields fuel-range hydrocarbon distillates containing open-chain oligomers at a high selectivity (>96%) including, e.g., normal paraffins and isoparaffins. Fuel-range distillates have a low concentration of aromatics (<4 wt %) that renders these distillates ideally suited to production of alternative (including renewable) hydrocarbon fuels such as jet fuels and diesel fuels, or other low aromatic fuels and fuel blend stocks. In other modes of operation, concentrations of aromatics >4% may be obtained. As shown in the figure, ethylene in the ethylene-containing feedstock may be derived from such fossil fuel sources such as petroleum, coal, and natural gas. Ethylene may also be obtained from bio-based sources and/or alternative sources including, but not limited to, e.g., sugars and sugar derivatives such as ethanol, starches and starch derivatives such as starch ethanol, and lignocellulose and lignocellulosic derivatives such as lignocellulosic ethanol.

Ethanol as an Ethylene Source

Ethylene used in ethylene-containing feedstocks in the first oligomerization step/stage may be derived from ethanol. Ethanol may be derived from any known thermal or biological process. Pure ethanol is not required. For example, in some applications, aqueous ethanol may be used to lower production costs. In some applications, concentrations of ethanol of about 50% or greater ethanol in water may be used. In some applications, the source of aqueous ethanol may be obtained from a fermentation purified via a "Beer Column" distillation. In some applications, the concentration of ethanol may be between 20% and 100%.

Ethanol or ethanol-containing feedstocks may be optionally fed to a dehydration reactor optionally with an inert gas such as $N_2$, pre-heated to a selected reaction temperature, and passed over a dehydration catalyst (e.g., alumina, modified alumina, silicoaluminate, modified silicoaluminate, and other catalysts) at a temperature and pressure sufficient to carry out the dehydration reaction that forms ethylene. Conditions depend on the catalyst used, which may be determined using methods known to those of ordinary skill in the art. This process is practiced industrially. No limitations are intended.

In various embodiments, ethanol may be introduced to the dehydration reactor at a weight hourly space velocity (WHSV) of between about 0.1 $h^{-1}$ to about 30 $h^{-1}$. In some embodiments, ethanol may be fed to the dehydration reactor at a WHSV value of between about 0.5 $h^{-1}$ to about 5 $h^{-1}$.

In some embodiments, the dehydration reactor may be operated at a temperature from about 200° C. to about 500° C. In some embodiments, the dehydration reactor may be operated at a temperature from about 300° C. to about 450° C. In some embodiments, the dehydration reactor may be operated at a pressure from about 0 psig to about 1200 psig. In some embodiments, the dehydration reactor may be operated at a pressure from about 0 psig to about 500 psig.

Ethanol conversion may vary depending on operating conditions and the selected catalyst from between about 10% and about 100%.

The ethylene-containing product may be purified to remove water, by-products, oxygen, and other impurities. Purification could include condensing water and purifying the product through a purifying medium such as silicas, molecular sieves, and carbons. The purified product may be collected or passed directly to the first oligomerization reactor.

Mixed alcohols with a carbon number from C1 to C4 and greater can be prepared from syngas over any of several catalysts. Certain catalysts, such as those containing rhodium, are selective for ethanol. Others, such as Co/Mo/sulfide, have higher selectivity to methanol, but on recycle of the methanol selectivity to ethanol increases. Mixed alcohols containing ethanol are easily dehydrated by methods discussed above to form an ethylene-containing feed for the two-step process or two-stage system.

Methanol as an Ethylene Source

The process for conversion of methanol to olefins (MTO) can be used to form mixtures of predominately ethylene and propylene at high yields. Selectivities to C2 to C4 olefins of 96% have been reported. MTO can be a source of ethylene-containing feed for the two-step process or two-stage system. Methanol for this process could be obtained from any source, the major source being from syngas.

1$^{st}$ Oligomerization Process

C2 to Oligs

Ethylene or an ethylene-containing feed from any source may be fed to a first oligomerization reactor or group of reactors, optionally with an inert gas such as $N_2$, pre-heated to selected reaction temperatures, and passed over a first oligomerization catalyst (e.g., nickel on a silicoaluminate material support) at selected temperatures and pressures to carry out the first oligomerization step of a two-step process. Gaseous feeds may be passed through purifying media such as silicas and/or molecular sieves to remove trace water and copper-based and other materials to remove trace oxygen.

In various embodiments, ethylene in the ethylene-containing feedstock may be introduced to the first oligomerization reactor at a weight hourly space velocity (WHSV) of between about 0.1 $h^{-1}$ to about 100 $h^{-1}$. In various embodiments, ethylene in the ethylene-containing feedstock may be introduced to the first oligomerization reactor at a WHSV value of between about 0.5 $h^{-1}$ to about 5 $h^{-1}$.

In some embodiments, first oligomerization reactor may be operated at a temperature from about 40° C. to about 220° C. In some embodiments, first oligomerization reactor may be operated at a temperature from about 80° C. to about 160° C. In some embodiments, first oligomerization reactor may be operated at a pressure from about 0 psig to about 1200 psig. In some embodiments, first oligomerization reactor may be operated at a pressure from about 100 psig to about 500 psig.

First oligomerization products may include light oligomers, and mixtures of intermediate molecular weight normal and branched olefins. Carbon number may be primarily from about C4 to about C8. In one embodiment, the hydrocarbon product may include 70% C4, 27% C6, and 3% C8 hydrocarbons including, e.g., butenes, hexenes, and octenes. Hydrocarbon products may be collected or passed directly to the second oligomerization step of the two-step process.

The first oligomerization step may be conducted in one reactor, in multiple sequential reactors, and/or in parallel reactors. Multiple reactors can be used, for example, to manage process heat. Conversion of ethylene in each reactor varies with operating conditions from between about 10% conversion to about 100% conversion. Ethylene may be recycled to any of the reactors to increase overall conversion.

2$^{nd}$ Oligomerization Process

Oligomers in the first oligomerization product may be converted in a second oligomerization step of the two-step process over selected solid acid catalysts to mixtures of higher molecular weight oligomers including, e.g., branched open-chain olefins with a carbon number in the distillate range from about C8 to about C23. Solid acid catalysts include, but are not limited to, e.g., crystalline zeolite catalysts, amorphous silicoaluminate catalysts, acid form cation exchange resins, such as Amberlyst 70, and other acid catalysts. In some embodiments, aromatic hydrocarbons may be formed at a concentration below about 4 wt %. In some embodiments, aromatic hydrocarbons may be formed at a concentration between 4 and 10%. In some embodiments, aromatic hydrocarbons may be formed at a concentration between 10 and 20%. However, concentration of aromatics can be tailored to any desired concentration under appropriate conditions. Temperatures may be selected that are sufficiently high to initiate and promote oligomerization reactions but sufficiently low to minimize and avoid coking, and to minimize aromatization. In some embodiments, temperatures are selected between about 150° C. to about 350° C. In some embodiments, temperatures are selected between about 200° C. to about 280° C.

In some embodiments, the second oligomerization reactor may be operated at a pressure from about 50 psig to about 1000 psig. In some embodiments, the second oligomerization reactor may be operated at a pressure from about 100 psig to about 500 psig. In various embodiments, the first oligomerization product may be introduced to the second oligomerization reactor at a weight hourly space velocity (WHSV) of between about 0.1 $h^{-1}$ to about 100 $h^{-1}$. In various embodiments, the first oligomerization product may be fed to the second oligomerization reactor at a WHSV value of between about 0.5 $h^{-1}$ to about 10 $h^{-1}$. In some embodiments, the second oligomerization product may be processed in post-processing steps described below. No limitations are intended.

Two-Stage Oligomerization System

Figure 2:
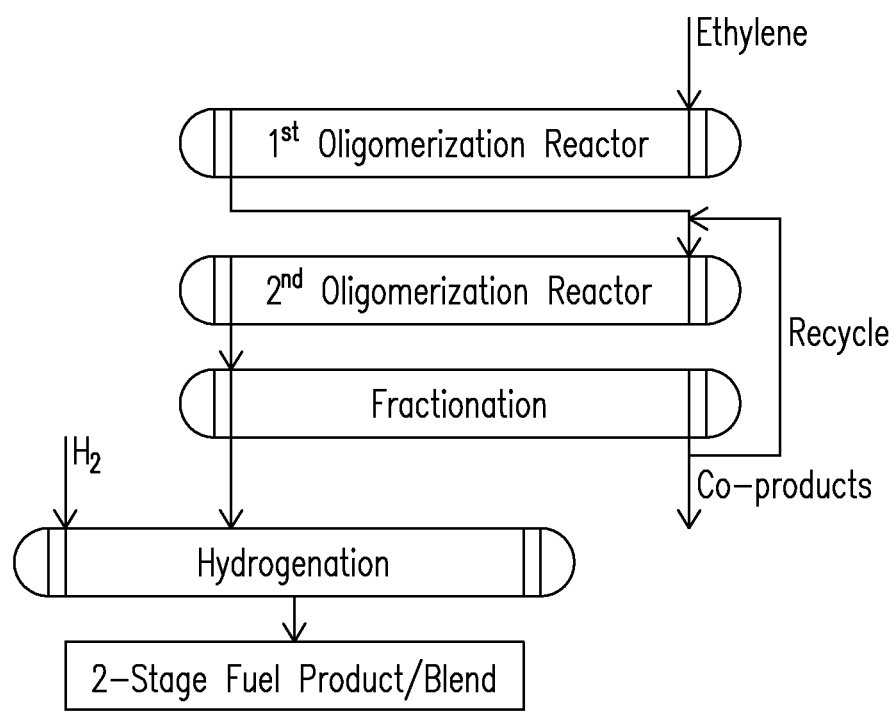
FIG. 2 shows a two-stage system for conversion of ethylene-containing feedstocks into fuel-range hydrocarbons for production of alternative (including renewable) hydrocarbon fuels.

FIG. 2 shows an exemplary reactor system of a two-stage oligomerization design for catalytic conversion of ethylene-containing feedstocks or an ethylene precursor feedstock such as ethanol (or ethanol-containing feedstocks) into fuel-range hydrocarbons suitable for production of alternative hydrocarbon fuels. Each reactor or stage may be charged with a selected catalyst.

[Ethanol Conversion]

The system may include a dehydration reactor as a first stage when ethanol-containing feedstocks are used as an ethylene precursor. Dehydration reactor may be charged with a solid acid dehydration catalyst such as alumina, modified alumina, crystalline or amorphous silicoaluminate, modified silicoaluminate, and other catalysts. The ethanol-containing feedstock may be introduced into dehydration reactor as a liquid feed at a WHSV value of between about 0.1 $h^{-1}$ and about 30 $h^{-1}$. Dehydration reactor may be operated at a dehydration temperature of about 200° C. to about 500° C. and a pressure of between about 0 psig to about 1200 psig. Ethanol concentrations may be in the range of 20 to 100 wt %. Preferred conditions are dependent on the catalyst and size of the reactor and are known to those skilled in the art. For the purposes of demonstrating this invention, a preferred WHSV is 0.5 $h^{-1}$ to 5 $h^{-1}$, a preferred temperature is 300° C. to 450° C., and a preferred pressure is 0 psig to 500 psig. Dehydration reactor may yield a mixed phase product containing predominately gaseous ethylene and a liquid waste water phase.

The ethylene-containing product obtained from dehydration reactor may require several cleanup steps performed in separate reactors or stages prior to being introduced to first oligomerization reactor or stage described hereafter. Cleanup steps may include a condensation step performed in a condensation stage (not shown) to remove liquids and adsorbent stages that remove trace water, organics, and oxygen impurities. Purified ethylene produced by this system is the ethylene-containing feedstock that feeds the first oligomerization system.

[First Oligomerization]

The system may also include a first oligomerization reactor or stage. Ethylene-containing feedstock, such as that obtained from dehydration reactor, may be introduced to first oligomerization reactor. First oligomerization reactor may be charged with a selected oligomerization catalyst such as Ni on a silicoaluminate. Ethylene-containing feedstock may be introduced, e.g., as a gas feed into first oligomerization reactor at a WHSV value of between 0.1 $h^{-1}$ to about 100 $h^{-1}$. First oligomerization reactor may be operated at a temperature of between about 40° C. and 220° C. and a pressure of between 0 psig and about 1200 psig. A preferred temperature is from about 80° C. to about 160° C. A preferred pressure is from about 100 psig to about 500 psig. A preferred WHSV is from about 0.5 $h^{-1}$ to about 5 $h^{-1}$. First oligomerization reactor or stage may yield a first oligomerization product containing predominately C4, C6, and C8 oligomerization products.

In some embodiments, one or more reactors may be operated as first oligomerization reactors in series and/or in parallel, each operated, for example, at a lower conversion rate to control exotherms, but configured to provide high overall ethylene conversion.

In some embodiments, ethanol dehydration and first oligomerization may be operated independently or operated as integrated flow reactors.

In some embodiments, residual liquids may be removed from the first oligomerization product in a liquid/gas (L/G) separator (not shown) prior to being introduced in a feed to second oligomerization stage.

[Second Oligomerization]

The system may also include a second oligomerization reactor or stage. Second oligomerization reactor or stage may be charged with a second oligomerization catalyst such as a solid acid including, e.g., a crystalline or amorphous silicoaluminate described previously herein. First oligomerization product obtained from first oligomerization reactor or stage may be introduced to second oligomerization reactor or stage. Second oligomerization reactor or stage may be operated at a WHSV of between 0.1 $h^{-1}$ and 100 $h^{-1}$, a temperature of between about 150° C. and about 350° C., and a pressure of between 50 psig and about 1000 psig. A preferred condition is a WHSV of about 0.5 $h^{-1}$ and 10 $h^{-1}$, a temperature of 200° C. to 280° C., and a pressure of from about 100 psig to about 500 psig. In operation, first oligomerization product may be pre-heated to a vapor, e.g., at a temperature of about 200° C. to about 280° C.

Second oligomerization reactor or stage may yield a second oligomerization product containing olefinic fuel-range hydrocarbons. Reactions are exothermic. Heat obtained in second oligomerization reactor or stage may be collected for use in pre-heating the feed, or elsewhere. In some embodiments, the second stage product may be further processed in post-processing stages, described below. No limitations are intended.

Post-Processing

Oligomers (about C4 to about C23) obtained from the two-step process or two-stage system may be subjected to optional post-processing process steps or system stages including, e.g., fractionation, recycling, aromatization, alkylation, olefin metathesis, and/or hydrotreatment described further hereafter. Other post-processing operations may also be used and no limitations are intended.

Fractionation

Hydrocarbon products obtained from the second oligomerization reactor may include linear and branched olefin hydrocarbons with a carbon number from about C4 to about C23. Fractionation, e.g., by distillation or by flash evaporation, may be conducted at a determined fractionation temperature or boiling point cut-off to separate out various boiling point fractions appropriate to a desired fuel product and to collect olefinic light products for further processing. Fractionation may be conducted as a process step or in a selected system stage.

In some embodiments, fractionation may be conducted prior to hydrogenation to form light olefin distillates and olefin heavy products that can be processed further independently.

The light fraction may be recycled to the first or second oligomerization step or stage for conversion to hydrocarbon fuels, thereby increasing yield to products in the distillate range. The light fraction may be sent to a third reactor for conversion to aromatic hydrocarbons, which may in turn be used for fuel blending or hydrogenated to afford a cyclic paraffin blend stock. The light fraction could be combined with an aromatic-containing process stream to alkylate the aromatics to a higher-boiling product, which may in turn be used for fuel blending or hydrogenated to afford a cyclic paraffin blend stock. Light fractions can be reformed to generate hydrogen gas for hydrotreating operations. Light fractions can be used as a feed to an olefin metathesis reactor to make other olefin products. Distillate olefin fractions can be in any or all of the jet, diesel, or other fuel ranges. Fractions can be hydrogenated to provide paraffin and iso-paraffin fuels or fuel blend stocks. Heavy olefin fractions boiling above a desired fuel range can be cracked over selected catalysts to produce lower boiling fractions. Heavy fractions containing olefins may be passed with ethylene over a metathesis catalyst such as a tungsten-based or molybdenum-based catalyst to form lower molecular weight olefinic fuel-range hydrocarbon products that can be recycled or fractionated to produce fuel products as described herein.

In another embodiment, fractionation can be conducted upon completion of all other post-processing in order to more accurately control the composition of the collected fractions. Such control might be desirable, for example, if a specific boiling point range were desired to meet the specifications of a desired fuel type.

Recycling

Recycling can be performed as a process step or in a selected system stage. For example, unreacted ethylene and/or a light fraction may be recycled back to either the first or second oligomerization steps or stages to increase carbon number and product yield in the desired distillate range. For example, light products from fractionation of second oligomerization product may be recycled by combining a quantity between 0% and 100% with first oligomerization reactor product to make a new feed that can then be introduced to the second oligomerization reactor. Fuel-range hydrocarbons obtained from oligomerization of recycled light fraction hydrocarbons may include, but are not limited to, e.g., a majority composition of linear and branched C8 to C23 olefins and a minor composition of aromatics. For example, the present invention produces C8 and greater carbon-number products at a selectivity greater than or equal to about 75% by weight on average and C10 and greater carbon-number products at a selectivity greater than or equal to about 55% by weight on average. Selectivity values after one recycle of the light fraction from the second oligomerization are C8 of about 90% and C10 of about 70%.

Aromatics are formed at 4%. Additional recycling will further increase selectivity to the desired carbon number or boiling point range. Second oligomerization products obtained from recycled materials may be subjected to any post-processing method. No limitations are intended.

Aromatization

Light olefins obtained from fractionation of the second oligomerization hydrocarbon product may be fed to a reactor for conversion to aromatic compounds. Aromatic compounds may be used directly as fuels, in fuel blend stocks, and/or as fuel precursors. Light olefins may be fed to a reactor optionally with an inert gas such as $N_2$, pre-heated to selected reaction temperatures, and passed over selected aromatization catalysts at temperatures and pressures sufficient to carry out aromatization. Aromatization catalysts employed in the reactor may include, but are not limited to, zeolites such as H-ZSM-5, or metal-exchanged zeolites such as potassium exchanged H-ZSM-5. No limitations are intended. Aromatization operation can be conducted as a process step or in a selected system stage.

In various embodiments, feed may be introduced to the aromatization reactor at a WHSV of between about $0.1\ h^{-1}$ to about $100\ h^{-1}$. In some embodiments, feed may be introduced to the aromatization reactor at a WHSV value of between about $0.5\ h^{-1}$ to about $5\ h^{-1}$.

In some embodiments, the aromatization reactor may be operated at a temperature selected between about 250° C. and about 500° C. In some embodiments, the aromatization reactor may be operated at a temperature selected between about 300° C. and about 400° C. In some embodiments, the aromatization reactor may be operated at a pressure selected between about 0 psig and about 1000 psig. In some embodiments, the aromatization reactor may be operated at a pressure between about 50 psig and about 500 psig.

Alkylation

Aromatic products, obtained for example from the aromatization reactor, the one-step product, or any other sources, may be mixed with an alkylating olefin stream, comprising ethylene, first oligomerization products, or olefinic light products from fractionation of the second oligomerization product, and introduced to an alkylation reactor to increase the molecular weight of the aromatic products in order to increase yield in a desired distillate range. Alkylated aromatic compounds so obtained may be used directly as fuels, in fuel blend stocks, and/or as fuel precursors, before or after fractionation and/or hydrotreating. Feedstock conversion varies with operating conditions between about 10 to about 100%.

Aromatic products and alkylating olefins may be fed to a reactor optionally with an inert gas such as $N_2$, pre-heated to selected reaction temperatures, and passed over selected alkylation catalysts at temperatures and pressures sufficient to carry out alkylation. Alkylation catalysts employed in the reactor may include, but are not limited to, strong acid catalysts, such as zeolites including H-ZSM-5 or Beta zeolite. Alkylation operation can be conducted as a process step or in a selected system stage.

In various embodiments, feed may be introduced to the alkylation reactor at a WHSV of between about $0.1\ h^{-1}$ to about $100\ h^{-1}$. In some embodiments, feed may be introduced to the alkylation reactor at a WHSV value of between about $0.5\ h^{-1}$ to about $5\ h^{-1}$.

In some embodiments, the alkylation reactor may be operated at a temperature selected between about 50° C. and about 500° C. In some embodiments, the alkylation reactor may be operated at a temperature selected between about 100° C. and about 350° C. In some embodiments, the alkylation reactor may be operated at a pressure selected between about 50 psig and about 2500 psig. In some embodiments, the alkylation reactor may be operated at a pressure between about 200 psig and about 600 psig.

Olefin Metathesis

Light or heavy olefin products obtained from fractionation of hydrocarbon products from the second oligomerization step or stage may be co-fed with ethylene to a reactor containing an olefin metathesis catalyst for conversion to shorter-chain alpha-olefins. Olefin metathesis catalysts include, but are not limited to, W or Mo on alumina. Metathesis reactions fragment and/or redistribute carbon-carbon double bonds in the olefins. For example, olefin products may be fed to the metathesis reactor with ethylene and optionally with an inert gas such as $N_2$, pre-heated to reaction temperature, and passed over the metathesis catalyst at a temperature and pressure sufficient to carry out the metathesis reactions that yield lighter olefin products. This operation can be conducted as a process step or system stage.

In various embodiments, feed may be introduced to the metathesis reactor at a WHSV of between about $0.1\ h^{-1}$ to about $100\ h^{-1}$. In some embodiments, feed may be introduced to the metathesis reactor at a WHSV value of between about $0.5\ h^{-1}$ and about $5\ h^{-1}$.

In some embodiments, metathesis reactor may be operated at a temperature selected from about 50° C. to about 500° C. In some embodiments, metathesis reactor may be operated at a temperature selected from about 100° C. to about 350° C.

In some embodiments, metathesis reactor may be operated at a pressure selected from about 50 psig to about 1000 psig. In some embodiments, metathesis reactor may be operated at a pressure from about 100 psig to about 500 psig.

Hydrocarbon products may be collected and further fractionated to obtain desired fuel-range hydrocarbons. Feedstock conversion varies with operating conditions between about 10% and about 100%.

Hydrotreatment

Hydrocarbon products from the second oligomerization step, fractions of those products, or products from other post-processing operations may be introduced as feeds to a hydrotreater and converted to saturated hydrocarbon fuels and fuel blend stocks. Hydrocarbon product feeds may be introduced to the hydrotreater optionally with an inert gas such as $N_2$ at selected feed rates, pre-heated to a selected reaction temperature, and passed over a catalyst at a temperature and pressure sufficient to carry out hydrogenation. Hydrogenation catalysts employed in the hydrotreater may include, but are not limited to, Pt on alumina, Pt on carbon, Ni on silica, and Raney-type catalysts including, but not limited to Raney Ni. Choice of catalyst depends, in part, on whether it is desirable to hydrogenate olefins (Pt) or both olefins and aromatics (Ni). Hydrotreating operation may be conducted as a process step or in a selected system stage.

In various embodiments, feed may be introduced to the hydrotreater at a WHSV of between about $0.1\ h^{-1}$ to about 100 h$^{-1}$. In some embodiments, feed may be introduced to the hydrotreater at a WHSV value of between about 0.5 h$^{-1}$ to about 10 h$^{-1}$.

In some embodiments, the hydrotreater may be operated at a temperature selected between about 100° C. and about 400° C. In some embodiments, the hydrotreater may be operated at a temperature selected between about 150° C. and about 350° C. In some embodiments, the hydrotreater may be operated at a pressure selected between about 100 psig and about 2000 psig. In some embodiments, the hydrotreater may be operated at a pressure between about 500 and about 1000 psig. Hydrotreater products may be collected or further fractionated to obtain a desired fuel such as jet, diesel, or gasoline or a fuel blend stock product. Feedstock conversion varies with operating conditions between about 10% and about 100%.

Reactors

Reactors may be of any type that provides contact between the selected feed or feedstock and the selected catalyst. In some embodiments, reactors may be of a fixed-bed type, but reactors are not intended to be limited. Reactors suitable for use include, but are not limited to, e.g., fixed-bed reactors, fluidized bed reactors, circulating fluid-bed reactors, batch reactors, flow reactors, sequential flow reactors, continuous stirred-tank reactors, sequential continuous stirred-tank reactors, batch-flow reactors, ebulated-bed reactors, packed-bed reactors, tubular reactors, multi-tubular reactors, sequential multitubular reactors, network reactors, heat-exchange reactors, gas-liquid reactors, gas-solid reactors, radial-flow reactors, reverse-flow reactors, ring reactors, moving bed reactors, catalytic reactors, chemical reactors, gas reactors, trickle-bed reactors, column reactors, batch reactors, N-dimensional reactors and N-phase reactors where N is a number of dimensions or phases, heated reactors, cooled reactors, including combinations and components of these various reactors.

The two-step process or two-stage system may be performed in concert with other processes or systems to produce alternate fuels not obtainable by other methods. One such process or system will now be described.

One-Step Oligomerization

Figure 3:
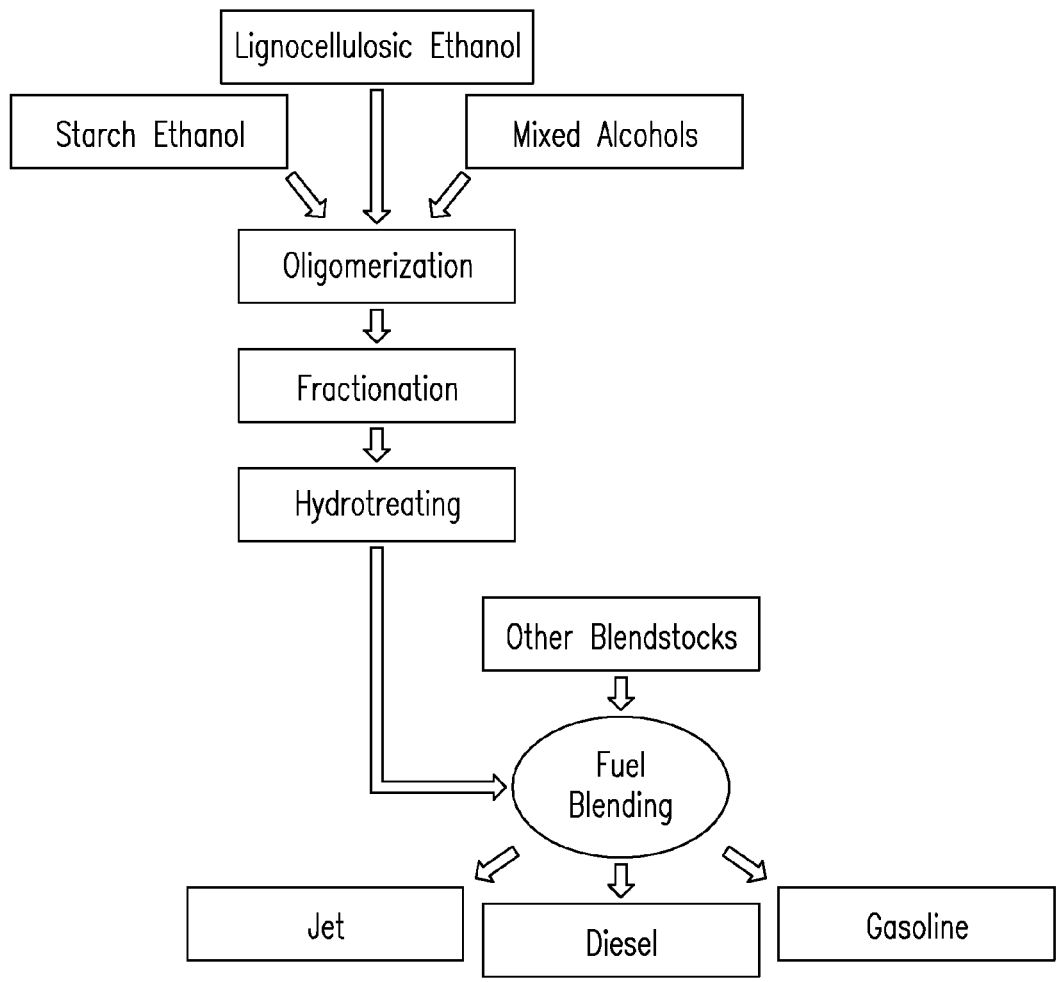
FIG. 3 shows an exemplary one-step process for conversion of an ethanol-containing feedstock into fuel-range hydrocarbons suitable for production of alternative (including renewable) hydrocarbon fuels, according to another embodiment of the process of the present invention.

FIG. 3 illustrates an exemplary one-step oligomerization process for catalytic conversion of ethanol-containing feedstocks that produces olefins (alkenes) and aromatics and other hydrocarbon products. Ethanol conversion over zeolite catalysts, such as HZSM-5, forms primarily diethyl ether through intermolecular dehydration at temperatures between 175° C. and 250° C. At higher temperatures of about 280° C., intramolecular dehydration forms ethylene. Above temperatures of 280° C., ethanol forms ethylene and ethylene undergoes reactions including, e.g., oligomerization, dehydrocyclization, hydrogenation, and cracking that form complex mixtures of hydrocarbon products including, e.g., paraffins, olefins, saturated cyclics, aromatics, and naphthalene with typical carbon numbers between C2 and C12. Product distribution depends on processing temperatures and catalyst. In some embodiments, zeolite catalysts may be used to convert ethanol to form a "clean" aromatic product containing no appreciable quantity of undesirable durene (1,2,4,5-tetramethylbenzene). In some embodiments, aromatics may be alkylated to form higher molecular weight hydrocarbons or may be hydrogenated (reduced) to produce oxygen-free cyclic hydrocarbons suitable for use in production of desired hydrocarbon fuels.

In some embodiments, temperatures are selected between about 280° C. to about 500° C. In some embodiments, temperatures are selected between about 300° C. to about 450° C. In some embodiments, the one-step reactor may be operated at a pressure from about 0 psig to about 1000 psig. In some embodiments, the one-step reactor may be operated at a pressure from about 50 psig to about 500 psig. In various embodiments, the ethanol-containing feed may be introduced to the one-step reactor at a WHSV of between about 0.1 h$^{-1}$ to about 100 h$^{-1}$. In various embodiments, the ethanol-containing feed may be introduced to the one-step reactor at a WHSV of between about 0.5 h$^{-1}$ to about 10 h$^{-1}$. In some embodiments, the one-step oligomerization product may be processed in post-processing steps described above. No limitations are intended.

One-Stage Oligomerization System

Figure 4:
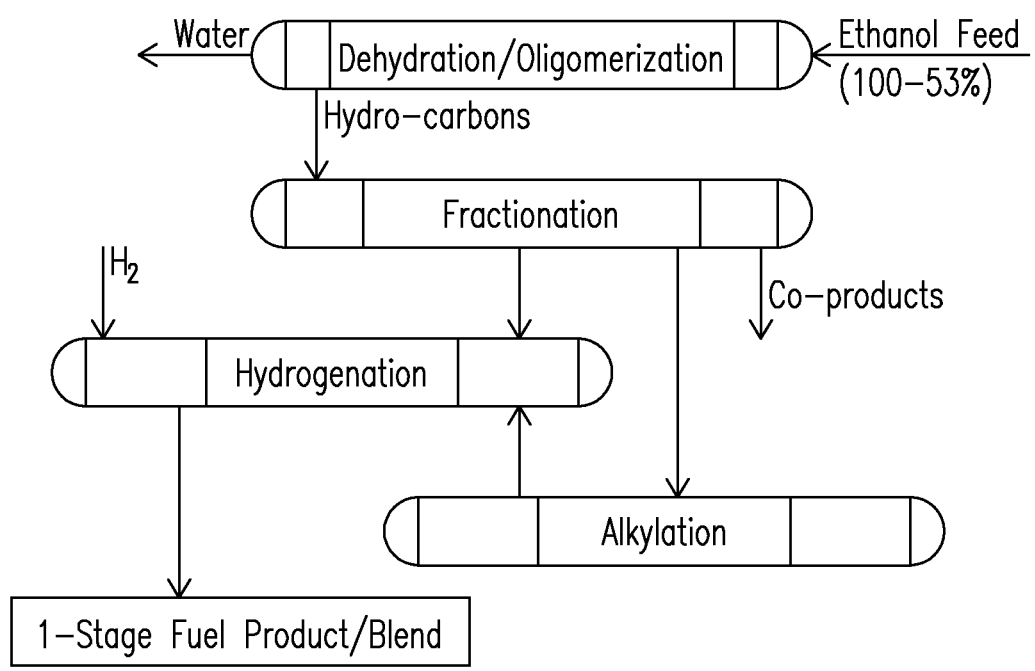
FIG. 4 shows a one-stage system for conversion of ethylene-containing feedstocks into fuel-range hydrocarbons for production of alternative (including renewable) hydrocarbon fuels.

FIG. 4 shows an exemplary reactor system of a one-stage oligomerization system for catalytic conversion of ethanol feedstock into olefins (alkenes) and aromatics suitable for production of alternative hydrocarbon fuels and fuel blend stocks. The dehydration/oligomerization reactor stage may be charged with a selected catalyst well known in the art. The catalyst could be silicoaluminates, silicoaluminophosphates, heteropoly acids, or others. Catalysts may be crystalline or amorphous.

In some embodiments, temperatures are selected between about 280° C. to about 500° C. In some embodiments, temperatures are selected between about 300° C. to about 450° C. In some embodiments, the one-step reactor may be operated at a pressure from about 0 psig to about 1000 psig. In some embodiments, the one-stage reactor may be operated at a pressure from about 50 psig to about 500 psig. In various embodiments, the ethanol-containing feed may be introduced to the one-stage reactor at a WHSV of between about 0.1 h$^{-1}$ to about 100 h$^{-1}$. In various embodiments, the ethanol-containing feed may be introduced to the one-stage reactor at a WHSV of between about 0.5 h$^{-1}$ to about 10 h$^{-1}$. In some embodiments, the one-stage oligomerization product may be processed in post-processing stages described above. No limitations are intended.

Dehydration/oligomerization stage may yield a mixed phase product containing predominately an organic liquid product phase and a liquid waste water phase. Optional post-processing stages can be conducted, including fractionation, alkylation, hydrogenation, and others as described above. No limitations are intended.

Combined Two-Step and One-Step Oligomerization

Figure 5:
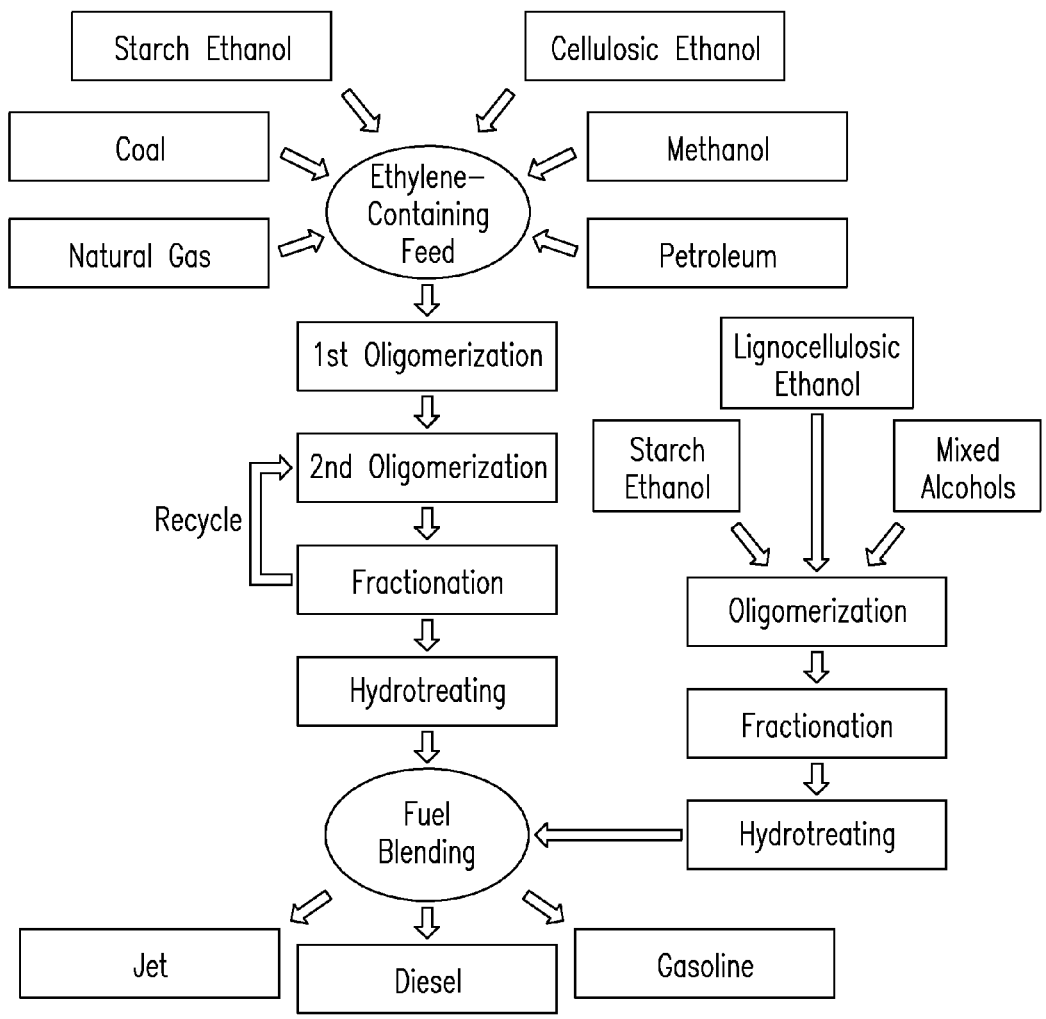
FIG. 5 shows an exemplary process for a combined one-step/two-step conversion of ethylene- and ethanol-containing feedstocks into fuel-range hydrocarbons suitable for production of alternative (including renewable) hydrocarbon fuels, according to yet another embodiment of the present invention.

FIG. 5 shows another exemplary process of the present invention that combines 2-step oligomerization processing for catalytic conversion of ethylene-containing feedstocks or feedstocks containing an ethylene precursor such as ethanol, and 1-step oligomerization processing for catalytic conversion of ethanol-containing feedstocks. The combined process yields distillates suitable for production of alternative hydrocarbon fuels. The combined process produces fuels and fuel blend stocks not available from either process independently nor from other processes known in the art. Likewise, the one-stage system may be combined with the two-stage system to define a combined system that produces fuels and fuel blend stocks not available from either system independently nor from other systems known in the art.

Ethylene-containing feeds and ethanol-containing feeds may be obtained from various sources detailed previously herein. Ethanol-containing feedstocks may be fed directly to a 1-step oligomerization system or process that converts the feedstock at selected temperatures and pressures to a complicated product mixture containing a majority aromatic products, naphthalenes, saturated cyclics, paraffins, and olefins. A majority of products may include carbon numbers between about C2 to about C12. The 1-step oligomerization system and process and optional post-processing are discussed in more detail above.

As another part of the present invention, ethylene-containing feeds may be fed to a two-step oligomerization system or process that converts the feedstock at selected temperatures and pressures to a product mixture containing normal and iso-paraffins. A majority of products may include carbon numbers between about C4 to about C23. The two-step oligomerization process and system and optional post-processing were discussed previously above.

As shown in the figure, products obtained from one-step processing, including optional post-processing steps, may be blended with products obtained from the two-step oligomerization, including optional post-processing steps, to form blended products. Blended products may form an alternative fuel or fuel feedstock suitable for production of various fuels including, but not limited to, e.g., gasoline, jet fuel, and diesel fuel. In one embodiment, optional hydrogenation may be conducted prior to blending. In other embodiments, optional hydrogenation may be conducted after blending. In other embodiments, optional fractionation may be conducted prior to blending. In yet other embodiments, fractionation may be conducted after blending. No limitations are intended.

Fuel Blending of Two-Step and One-Step Oligomerization Products

Figure 6:
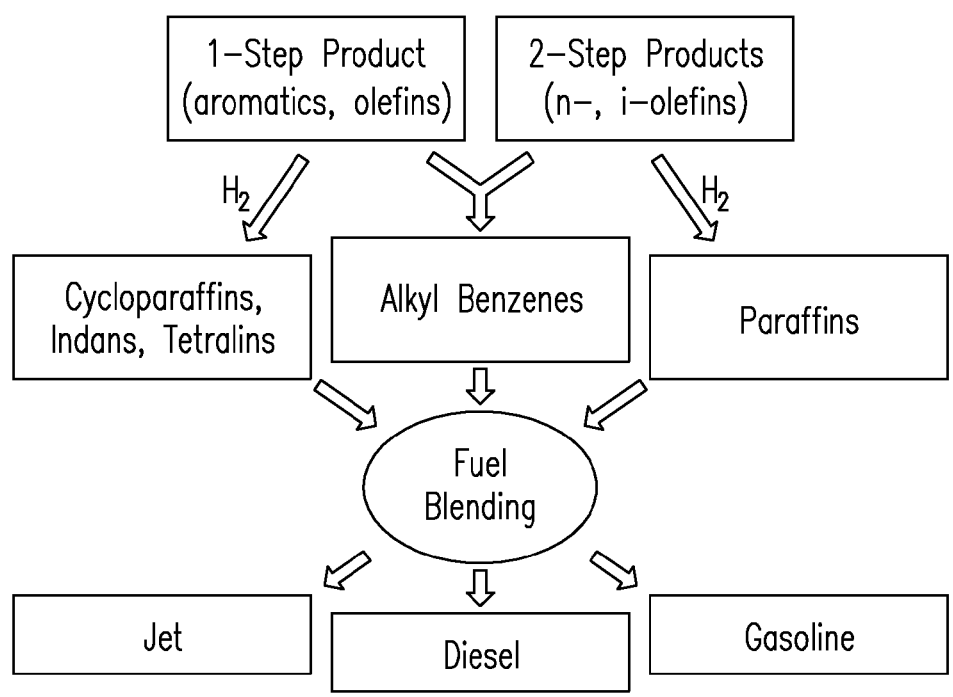
FIG. 6 shows an exemplary fuel-blending process for blending fuel-range hydrocarbons from selected distillates for production of alternative (including renewable) hydrocarbon fuels, according to still yet another embodiment of the present invention.

FIG. 6 shows an exemplary process for blending products obtained from two-step oligomerization processing and one-step oligomerization processing (FIG. 3) described previously hereinabove. As shown in the figure, one-step products and two-step products may be blended, fractionated, and hydrotreated. Or, one-step products and two-step products may be separately or individually fractionated and hydrotreated, and then blended. Hydrocarbon products may also be blended in various ways to produce various alternative fuels including, but not limited to, e.g., gasoline, jet fuel, and diesel fuel.

For example, two-step oligomerization products may include normal and branched olefins that when hydrotreated with hydrogen at selected temperatures and hydrogen gas pressures form paraffins including, n-paraffins and i-paraffins. One-step oligomerization products may include primarily olefins and aromatic hydrocarbons that when hydrotreated at selected temperatures and hydrogen gas pressures form cycloparaffins, indans, and tetralins. Aromatic content may be controlled by the extent or degree of hydrogenation of one-step products.

In some embodiments, light olefin products from two-step processing may be combined with aromatics from one-step processing to produce alkylated aromatics with a molecular weight higher than the feed aromatics and an increased yield in the desired fuel range.

In yet other embodiments, the light olefins outside the desired fuel range can be sent to an aromatization reactor to produce aromatics that could be combined with one-step products or subjected to further processing, including fuel blending, alkylation, or hydrotreating.

Hydrotreated product materials may be blended in selected ratios to produce desired fuels. Choice of processing options depends at least in part on the desired composition of the fuels to be produced. As shown in the figure, products obtained from one-step oligomerization and two-step oligomerization following further optional processing as described and hydrotreating may be blended in various ways to produce various alternative fuels including, but not limited to, e.g., gasoline, jet fuel, and diesel fuel.

Catalysts

[Ethanol Dehydration Catalyst]

Dehydration catalysts that convert ethanol to ethylene include, but are not limited to, e.g., silicoaluminate catalysts, aluminas, modified aluminas, and other solid acid catalysts. Alumina-based materials include BASF Al 3992 E ⅛". Silicoaluminate catalysts may have a crystalline structure such as beta zeolite, H-ZSM-5, and like materials. Silicoaluminate catalysts may also have an amorphous structure such as Grace 3111 and like materials. Silicoaluminate catalysts may be in the form of a powder (e.g., Grace 3111 and similar materials), or have an engineered form (e.g., Grace Davicat X-501 and similar materials). Silicoaluminate catalysts may be commercially obtained. Silicoaluminate catalysts may also be prepared from suitable Si-containing and Al-containing materials by methods known in the catalyst art. Prepared silicoaluminate catalysts may be calcined at temperatures between about 200° C. and about 900° C.

[First Oligomerization Catalyst].

A preferred catalyst for first step oligomerization may be nickel on a silicoaluminate material support. In some embodiments, nickel (Ni) concentration in the catalyst may be selected in the range from about 0.1 wt % to about 10 wt %. In some embodiments, nickel (Ni) concentration in the catalyst may be preferably selected in the range from about 0.2 wt % to about 3 wt %.

Silicoaluminate support may have a crystalline structure such as beta zeolite and like materials. Silicoaluminate support may also have an amorphous structure such as Grace 3111 and like materials. Support may be in the form of a powder (e.g., Grace 3111 and similar materials), or have an engineered form (e.g., Grace Davicat X501 and similar materials). Support may be commercially obtained or may be prepared from suitable Si-containing and Al-containing materials, such as sodium silicate and alumina and their precursors by such methods as sol-gel synthesis.

Catalyst supports may be calcined at a temperature between about 200° C. and about 900° C. In some embodiments, nickel may be incorporated into the catalyst support by batch or column ion exchange, impregnation, or similar methods before or after calcination. In some embodiments, the catalyst support may be ion-exchanged with a Group I or Group II salt such as sodium chloride or sodium nitrate before or after calcination. In some embodiments, the catalyst support may be treated with a Group I or Group II base such as sodium carbonate or sodium acetate to reduce or eliminate Brønsted acidity before or after calcination. Nickel may be incorporated into the catalyst support by batch or column ion exchange, impregnation, or similar methods before or after treatment with a Group I or II salt or base and before or after calcination. In some embodiments, the catalyst support may be treated with ammonium hydroxide, washed, and dried before nickel is incorporated by any method.

[Second Oligomerization Catalyst]

Catalysts for second stage oligomerization may be silicoaluminate catalysts or may be solid acid catalysts like Amberlyst 70. Silicoaluminate catalysts may have a crystalline structure such as beta zeolite, H-ZSM-5, and like materials. Silicoaluminate catalysts may also have an amorphous structure. Silicoaluminate catalysts may also be in the form of powders (e.g., Grace 3111 and similar materials), or have an engineered form (e.g., Grace Davicat X-501 and similar materials). Silicoaluminate catalysts may be commercially obtained. Silicoaluminate catalysts may also be prepared from suitable Si-containing and Al-containing materials by methods known to those of ordinary skill in the art. Prepared silicoaluminate catalysts may be calcined at temperatures between about 200° C. and about 900° C.

In some embodiments, the second oligomerization catalyst may include acid zeolites including, e.g., Y-zeolites, Beta-zeolites, ZSM-5 zeolites (e.g., H-ZSM-5), Mordenite zeolites, Ferrierite zeolites, Al-MCM-41 zeolites, MCM-48 zeolites, MCM-22 zeolites, SAPO-34 zeolites, Chabazite zeolites, and combinations of these acid zeolites.

In some embodiments, the solid acid may include a concentration of an acidic metal oxide and/or an acid zeolite of between about 10% and about 80% by weight.

[Aromatization Catalysts]

Aromatization catalysts employed in the reactor may include, but are not limited to solid acid catalysts, e.g., crystalline zeolites, or their ion-exchanged derivatives. In some embodiments, the aromatization catalyst may be a partially potassium-exchanged H-ZSM-5.

[Hydrogenation Catalyst]

Hydrogenation catalysts suitable for hydrotreating selected feeds may include, but are not limited to, e.g., metals supported on various solid supports. Catalyst metals include, but are not limited to, e.g., ruthenium (Ru), rhenium (Re), palladium (Pd), platinum (Pt), nickel (Ni), and combinations of these metals. Preferred metal supports include but are not limited to, e.g., carbon, titania ($TiO_2$), zirconia ($ZrO_2$), alumina ($Al_2O_3$), and silica ($SiO_2$). Solid supports may be impregnated with the selected metal by contacting the solid oxides with an aqueous solution containing the selected metal salt. Once impregnated, metal ions in solution may be reduced at a temperature of, e.g., 300° C. in hydrogen gas, which activates the catalyst for use. For supported-metal catalysts, metal concentrations may be from about 0.5% to about 10% by weight. Metal support concentrations may be between about 90% and about 99.5% by weight. Catalysts may be of the Raney type, including but not limited to Raney nickel.

In some embodiments, hydrogenation catalysts include, e.g., platinum on carbon, platinum on alumina, and nickel on silica.

In some embodiments, hydrogenation catalysts may include sulfide-containing (i.e., sulfided) catalysts or non-sulfide-containing (i.e., non-sulfided) catalysts.

[Olefin Metathesis]

Olefin metathesis catalysts include, but are not limited to, e.g., W or Mo on alumina.

Catalysts of the present invention may be regenerated in the presence of oxygen to remove any coke formed on the catalysts during operation by oxidation.

Applications

The present invention finds application in private, commercial, and military aviation and private, commercial, and military land transportation. Integration of processes allows production of higher renewable content fuels, with benefits for co-location on a single site such as infrastructure, utilities, heat and energy balance, and hydrogen production.

EXAMPLES

The following Examples provide a further understanding of the invention:

Example 1

Preparation of First Oligomerization Catalyst 2.96 g of boehmite-alumina powder (e.g., Catalog #23N4-80 DISPAL® boehmite-alumina powder, Sasol Ltd., Houston, Tex., USA) was mixed with 5.0 g of solid NaOH pellets with enough deionized water to make a 250 mL solution. The solution was stirred and heated to 50-70° C. for 2.5 hr until solids were dissolved. The hot solution was rapidly added to a mixture of 300.05 g of sodium silicate solution (e.g., 26 wt % $SiO_2$, Sigma-Aldrich, St. Louis, Mo., USA) and 1085.15 g of deionized water and stirred for about 5 minutes. 430 mL of a 1.4 M nitric acid solution was then added, which formed a gel. The gel was stirred at room temperature for 3 days to age the gel. The aged gel was then separated from the supernatant via centrifugation. Centrifuged solids were re-slurried in about 1.5 L of deionized water, heated to 60-70° C., and agitated for at least 1.5 hr. The centrifugation, re-slurry, and agitation cycle was repeated three more times. The gel was then washed in a Buchner filter until the wash water attained a pH of 7. The gel was dried overnight in the Buchner filter in a flow of air, then heated in air in a porcelain crucible from room temperature to 110° C. at a rate of 5° C./min. The dried gel was then held for 3 hours at 110° C. The material was raised to a temperature of 550° C. at a rate of 5° C./min and held at temperature for 3 hr to calcine the material, which produced a sodium silica-alumina gel with a nominal $SiO_2/Al_2O_3$ ratio of 50. After calcination, all of the sodium silica-alumina gel (26.36 g) was mixed with 5.92 g of $NiCl_2.6H_2O$ dissolved in about 200 mL of deionized water. The solution was vigorously stirred, heated to reflux, and left overnight. After cooling, solids were filtered and washed five times, each time with about 150 mL of hot deionized water. Solids were dried overnight in a vacuum filter with 110° C. air passing though the solids.

Example 2

Preparation of First Oligomerization Catalyst 20.00 g of a beta zeolite powder (e.g., Catalog #CP814-C, Zeolyst International, Malvern, Pa., USA) was mixed with about 200 mL of a solution containing 4.28 g of anhydrous $NiCl_2$ dissolved in deionized water. The mixture was stirred vigorously and heated to reflux overnight. After cooling, supernatant was decanted from the settled solids. Solids were transferred to a Millipore® filter with a 0.6 μm disc, slurried, and filtered several times with about 200 mL of hot deionized water, and dried overnight at 60° C. After drying, the material was heated from room temperature to 550° C. in flowing air and held for 2 hr at 550° C. to calcine and pelletize the material. Pellets were then returned to ambient temperature at a rate of 10° C./min. Pellets were ground and then sieved through a −35/+80 mesh filter and collected.

Example 3

Preparation of First Oligomerization Catalyst 20.00 g of a Si—Al powder (e.g., Davicat SIAL 3111 powder, W.R. Grace & Co., Columbia, Md., USA) was mixed with about 200 mL of a solution containing 13.22 g of anhydrous $NiCl_2$ dissolved in deionized water. The mixture was stirred vigorously and heated to reflux overnight in a flask. Upon cooling, contents of the flask were washed into a Millipore® filter with a 0.6 μm disc with deionized water, slurried, and filtered 12 times with about 150 mL of hot deionized water, and then dried overnight at 60° C. After drying, material was pelletized, ground, and sieved through a −35/+100 mesh filter and collected.

Example 4

Preparation of First Oligomerization Catalyst

The preparation of EXAMPLE 3 was repeated using W.R. Grace & Co. Davicat SIAL 3113 powder.

Example 5

Preparation of First Oligomerization Catalyst

The preparation of EXAMPLE 3 was repeated using W.R. Grace & Co. Davicat SIAL 3125 powder.

Example 6

Preparation of First Oligomerization Catalyst

A Ni-exchanged silica/alumina catalyst using W.R. Grace & Co. Davicat X501 catalyst support was prepared via a column exchange method using $NiCl_2$ as the precursor. Davicat X501 extrudate was ground and sieved to 30-60 mesh size then calcined in air at 550° C. for about 6 hours. 20 g of this material was placed in a 250 mL chromatography column and rinsed with DI water to create a well-packed column. Excess DI water was drained off and a solution made with 13.22 g of Aldrich 98% $NiCl_2$ and about 200 mL of DI water was poured into the reservoir of the chromatography column. Outlet flow rate was adjusted to about 0.25 mL/min. The exchange was continued until all of the Ni solution drained. The Ni-exchanged X501 was slurried out of the column with DI water to a Millipore filter assembly equipped with an 0.45 μm nylon filter disk. After the initial supernatant removal, two washes with about 200 mL of room temperature DI water and two additional washes with about 250 mL of hot DI water were conducted. The dissolved solids meter reading after the second hot water wash was 14 ppm. The Ni-exchanged X501 material was dried in a vacuum oven overnight at 60° C. The dried Ni-X501 material weighed 21.07 g and the Ni loading was determined by ICP to be 0.8 wt %.

Example 7

Preparation of First Oligomerization Catalyst

A Ni-exchanged silica/alumina catalyst using W.R. Grace & Co. Davicat X501 catalyst support is prepared via a column exchange method using $NiCl_2$ as the precursor. Davicat X501 extrudate (14.79 g) was pre-treated with a 28% ammonia solution overnight at room temperature, then D.I. water washed, and dried overnight at 105° C. The treated and dried support was then Ni-ion exchanged with 200 mL of a 6.2 wt % $NiCl_2$ solution via the column exchange method. The catalyst was washed with de-ionized water while on the column until washes contained 8 ppm solids, then dried in a 60° C. vacuum oven for two days. The catalyst was found to contain 1.26 wt % Ni by ICP analysis.

Example 8

Preparation of a Metathesis Catalyst 39.21 g of dried alumina spheres (e.g., Sasol 2.5/210, Hamburg, Germany) were impregnated with an aqueous solution of ammonium heptamolybdate (54.34% Mo) to produce a final loading of Mo in the alumina spheres of about 8 wt %. The impregnated spheres were dried at 120° C. and then calcined at 680° C. for 2 hrs.

Example 9

First Oligomerization, Test 1

EXAMPLE 9 demonstrates an exemplary first oligomerization process. The catalyst of EXAMPLE 3 was used. 1.42 g of the catalyst was loaded into a ⅜-inch (1.0 cm) O.D. stainless steel tube supported on a bed of quartz wool for flow reactor testing. A thermocouple was placed at the radial center near the bottom of the catalyst bed. Soda lime beads were positioned above the catalyst bed to preheat the feed gas. The catalyst was pretreated at 300° C. and 0 psig in $N_2$ flowing at 100 $cm^3$/min at room temperature and pressure (RTP) for 4 hr. The catalyst was then cooled to 85° C. and the pressure was set to 300 psig. A mixture of ethylene flowing at a rate of 36.7 $cm^3$/min (RTP) and $N_2$ flowing at a rate of 7.5 $cm^3$/min (RTP) was introduced to the reactor via separate externally calibrated mass flow controllers. The gas mixture was passed through a molecular sieve sorbent to remove water and a copper (Cu) sorbent to remove oxygen prior to entering the catalytic reactor. Introduction of the ethylene/$N_2$ mixture to the reactor was designated as time zero [i.e., Time-On-Stream (TOS)=0 hr]. At a TOS of 116 hr, ethylene conversion was determined to be 97%. Ethylene conversion was steady at 97% after 312 hr TOS. Reaction product was collected at system pressure in one of two parallel stainless steel vessels chilled to 10° C. to 12.5° C. Concentration of gases in the reactor effluent including ethylene, butenes and $N_2$ were determined using a Carle packed-column gas chromatograph equipped with an externally calibrated thermal conductivity detector. The gaseous reactor effluent was measured with a digital flow meter (e.g., Agilent, Santa Clara, Calif., USA). Moles of ethylene in the reactor effluent were determined via effluent flow rate and concentration of ethylene assuming an ideal gas effluent. Molar ethylene conversion was determined using Equation [1]:

$$\text{Conversion} = 100 * \frac{\text{Ethylene (in)} - \text{Ethylene (out)}}{\text{Ethylene (in)}} \quad [1]$$

Neat liquid products were analyzed with a gas chromatograph (e.g., Agilent, Santa Clara, Calif., USA) equipped with a mass-selective detector. Compounds in the liquid samples were categorized by carbon number (e.g. butenes, hexenes, etc.). Peak area corresponding to compounds categorized together were summed and divided by the total peak area of the chromatogram to determine relative concentration of each organic category as a function of carbon number. Liquid samples collected between a TOS of 116 hr and 312 hr consisted of 72% C4, 24% C6, 4% C8, and <1% C10+.

Example 10

First Oligomerization, Test 2

Figure 7:
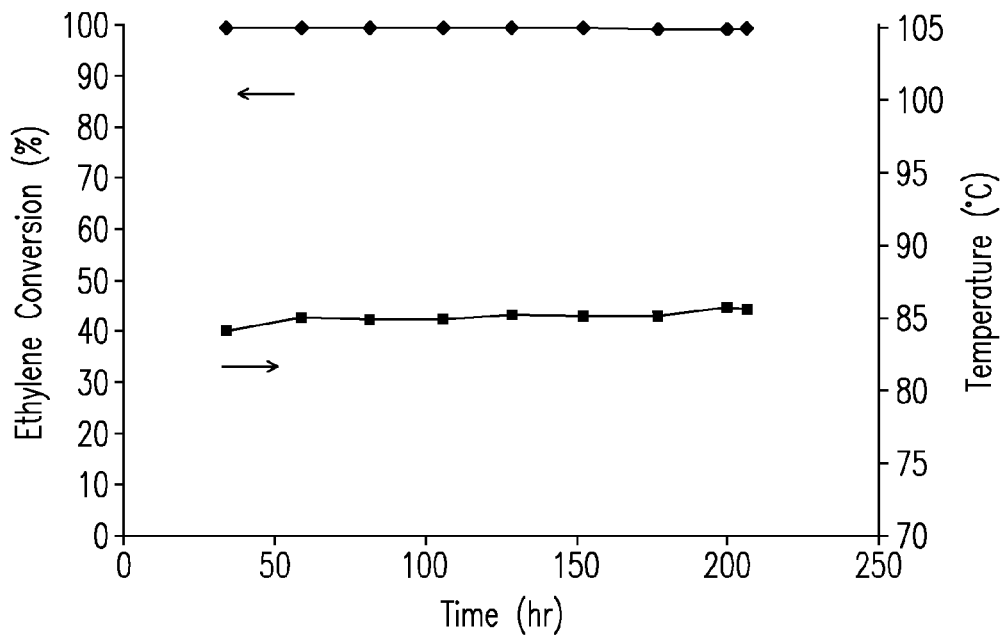
FIGS. 7-20 present selected experimental results.

1.40 g of the catalyst prepared in EXAMPLE 4 was loaded into the 3/8" (1.0 cm) tube reactor. The process conditions of EXAMPLE 9 were used. Ethylene conversion was 99% through a TOS of 206 hr (FIG. 7). Liquid samples collected between 129 TOS and 206 hr TOS consisted of 72% C4, 21% C6, 6% C8, and 2% C10+.

Example 11

First Oligomerization, Test 3

Figure 8:
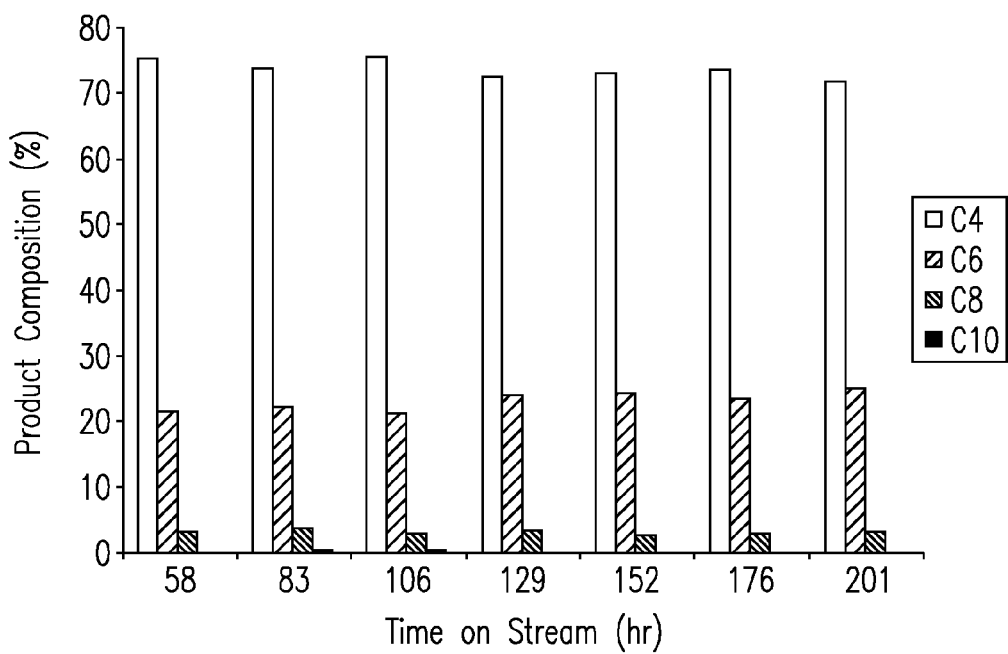

1.45 g of the catalyst prepared in EXAMPLE 5 was loaded into the 3/8" tube reactor. Process conditions of EXAMPLE 9 were used. Ethylene conversion increased from 66% to 95% over a TOS of 32 hr to 83 hr. Ethylene conversion then remained steady at 95% to 98% up to a TOS of 201 hr. As shown in FIG. 8, liquid samples had a steady composition of approximately 73% C4, 24% C6, 3% C8, and <1% C10+.

Example 12

First Oligomerization, Test 4

1.40 g of the catalyst prepared in EXAMPLE 3 was loaded into a 3/8" (1.0 cm) tube reactor. Process conditions of EXAMPLE 9 were used. At 1153 hr TOS, ethylene conversion was 51%. Liquid samples collected at 1153 hr TOS consisted of 66% C4, 30% C6, and 3% C8. At 1154 hr TOS, the catalyst was regenerated by lowering the reactor pressure to 0 psig, raising the temperature of the catalyst bed to 300° C. and passing 100 cm$^3$/min of N$_2$ over the catalyst for 4 hr. After reactivation, reactor temperature was lowered to 85° C., pressurized to 300 psig, and the reaction mixture was reintroduced to the reactor. After reactivation, ethylene conversion was measured to be 93-98% between 1183-1256 hr TOS. Liquid samples collected between 1183-1256 hr TOS averaged 68% C4, 29% C6, and 4% C8. From 1256 hr TOS to termination of the run at 2247 hr TOS, two more regenerations were conducted. Ethylene conversion after final regeneration was 44-45%. Liquid samples collected between 1256 TOS and 2247 hr TOS were similar in relative organic compound concentration of 67% C4, 29% C6, 3% C8, and 1% C10+. A total of about 2.9 L oligomerized product was collected over the 2247 hr run.

Example 13

Second Oligomerization, Test 1

Figure 9A:
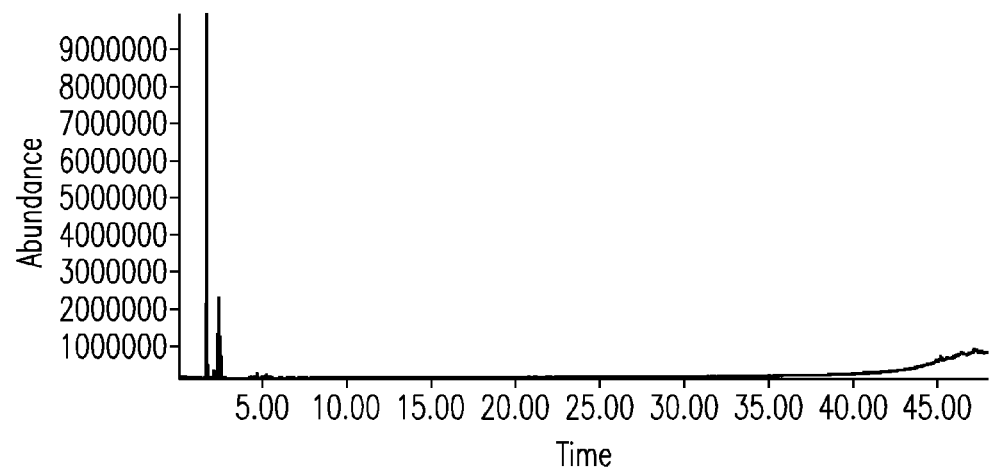
Figure 9B:
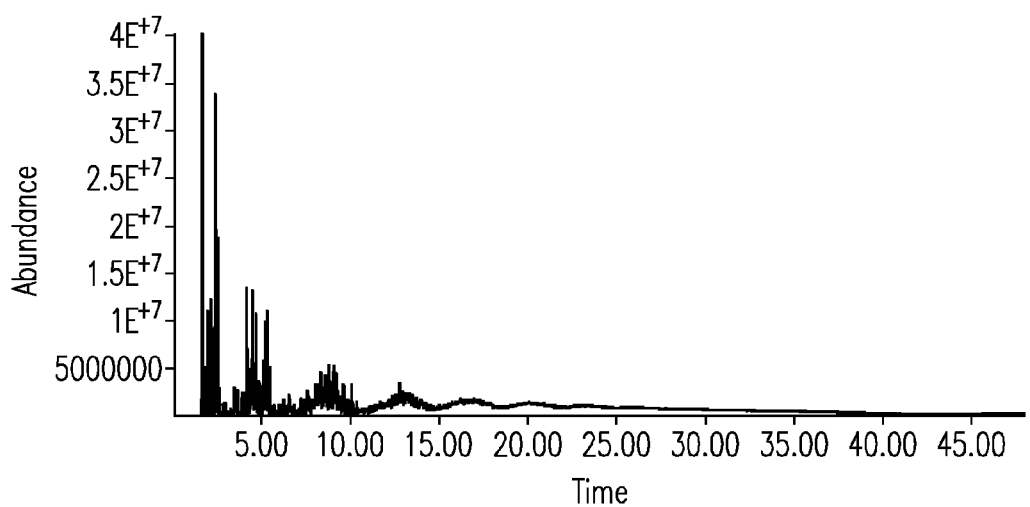
Figure 10:
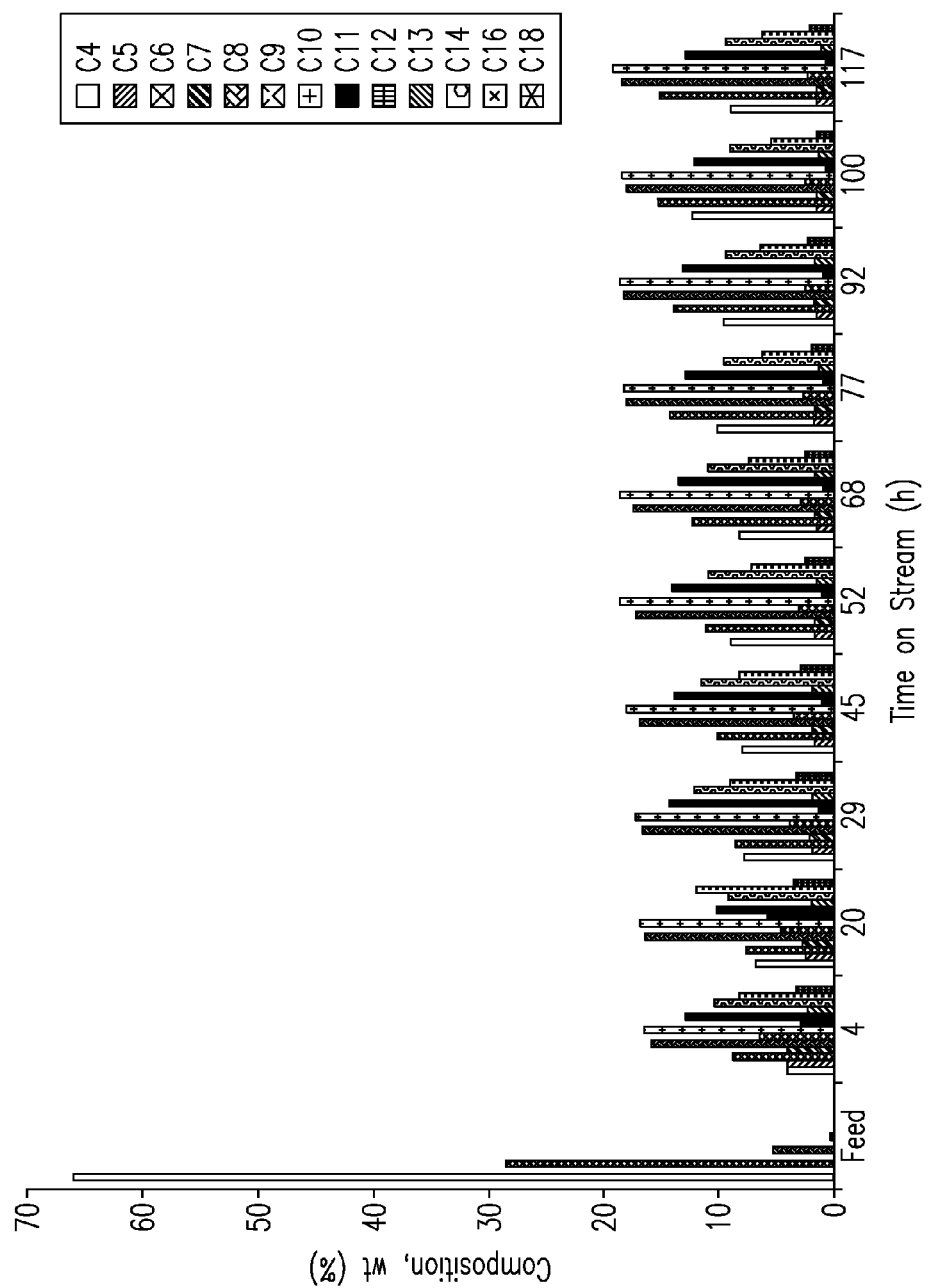

EXAMPLE 13 demonstrates conversion of a first oligomerization product to fuel-range hydrocarbons in a second oligomerization reactor. 1.64 g of W.R. Grace & Co. Davicat 3111 (−35/+100) mesh which had been calcined at 400° C. for 2 hrs in air was loaded in a 3/8" (1.0 cm) O.D. stainless steel tube reactor for reaction testing. Liquid produced during a portion of the test described in EXAMPLE 12 was fed to the top of the reactor at 0.1 mL/min. N$_2$ was fed to the top of the reactor as a carrier gas at a flow rate of 10 cm$^3$/min. The pressure of the reactor was maintained at a nominal value of 300 psig. Reactor temperature was monitored via a thermocouple placed at the radial center near the bottom of the catalyst bed. Temperature was maintained at 225° C. Liquid feed and reactor products were analyzed neat with a gas chromatograph (e.g., Agilent, Santa Clara, Calif., USA) equipped with a mass-selective detector. Compounds in the liquid samples were categorized by carbon number (e.g. butenes, hexenes, etc.). Peak area of compounds categorized together were summed and divided by the total peak area of the chromatogram to determine the relative concentration of each organic category as a function of carbon number. FIG. 9a shows typical GC/MS data for the first oligomerization product used as feed to the top of the second oligomerization reactor, and the second oligomerization product collected from the bottom of the reactor (FIG. 9b). Results demonstrate conversion of light olefins in the feed to heavier olefins in the product. In FIG. 10, the carbon number distribution of feed and product samples taken over the course of 117 hours TOS demonstrates stable production of fuel-range hydrocarbons.

Example 14

Second Oligomerization, Test 2

EXAMPLE 14 demonstrates the effect of temperature on the conversion of first oligomerization products to fuel-range hydrocarbons in a second oligomerization reactor. Testing and analysis was conducted as described in EXAMPLE 13. H-Beta zeolite (e.g., −30/+100 mesh zeolite, Guild Associates, Dublin, Ohio, USA) was calcined ex-situ in air at a temperature of 550° C. for 3 hr. 0.50 g of the calcined zeolite was loaded into the tube reactor. Feed was introduced to the reactor at a rate of 0.05 mL/min. A carrier gas of nitrogen (N$_2$) was fed to the reactor at a flow rate of 7.4 cm$^3$/min. The reactor was maintained at a nominal pressure of 300 psig. Temperature of the reactor was periodically increased. Liquid product was collected at system pressure in condensers chilled to a temperature of 10° C. TABLE 1 reports the reactor bed temperature and concentration of organic species as a function of carbon number for liquid samples at each reaction temperature.

TABLE 1 compares second oligomerization reactor bed temperature and concentration of organic species as a function of carbon number for tests with H-Beta zeolite catalyst.

| Composition by Carbon No. | Reactor Temperature, ° C. | | | | | | |
|---|---|---|---|---|---|---|---|
| | 200 | 225 | 250 | 275 | 300 | 325 | 350 |
| C4 | 9% | 8% | 7% | 6% | 7% | 7% | 8% |
| C5 | 1% | 2% | 2% | 3% | 3% | 3% | 2% |
| C6 | 19% | 17% | 17% | 16% | 19% | 18% | 25% |
| C7 | 1% | 2% | 2% | 3% | 3% | 4% | 2% |
| C8 | 20% | 20% | 20% | 21% | 23% | 23% | 26% |
| C9 | 2% | 2% | 3% | 3% | 2% | 3% | 1% |
| C10 | 20% | 19% | 20% | 20% | 20% | 19% | 19% |
| C11 | 1% | 1% | 1% | 1% | 1% | 1% | 0% |
| C12 | 12% | 12% | 12% | 12% | 11% | 10% | 8% |
| C13 | 1% | 2% | 2% | 2% | 2% | 2% | 1% |
| C14 | 8% | 8% | 8% | 8% | 6% | 6% | 4% |
| C16 | 5% | 2% | 5% | 5% | 3% | 3% | 2% |

TABLE 1-continued compares second oligomerization reactor bed temperature and concentration of organic species as a function of carbon number for tests with H-Beta zeolite catalyst.

| Composition by Carbon | Reactor Temperature, ° C. | | | | | | |
|---|---|---|---|---|---|---|---|
| No. | 200 | 225 | 250 | 275 | 300 | 325 | 350 |
| C18 | 2% | 4% | 1% | 1% | | | |
| Yield C8+ | 69% | 70% | 70% | 71% | 67% | 66% | 61% |
| Yield C10+ | 48% | 48% | 48% | 48% | 42% | 41% | 35% |

Figure 11:
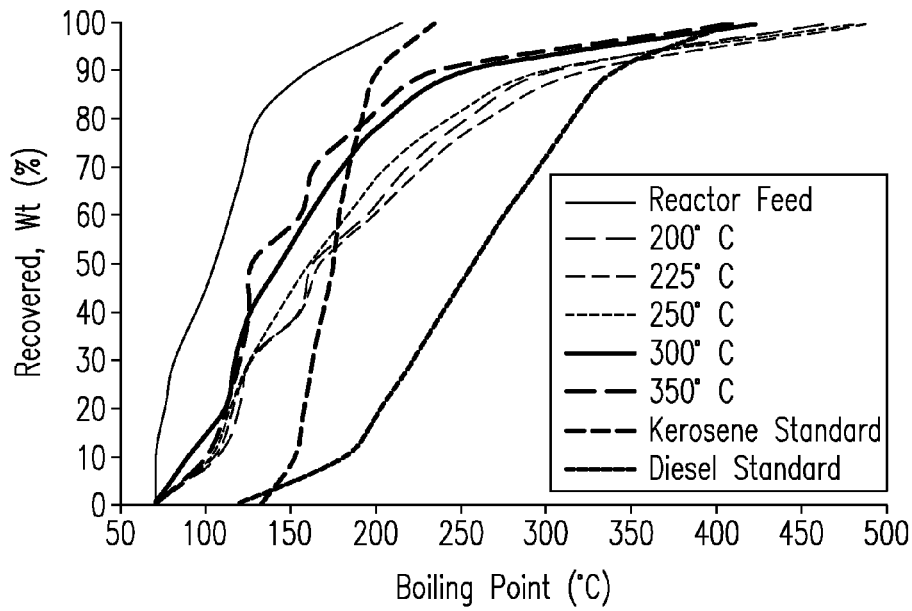
Figure 12:
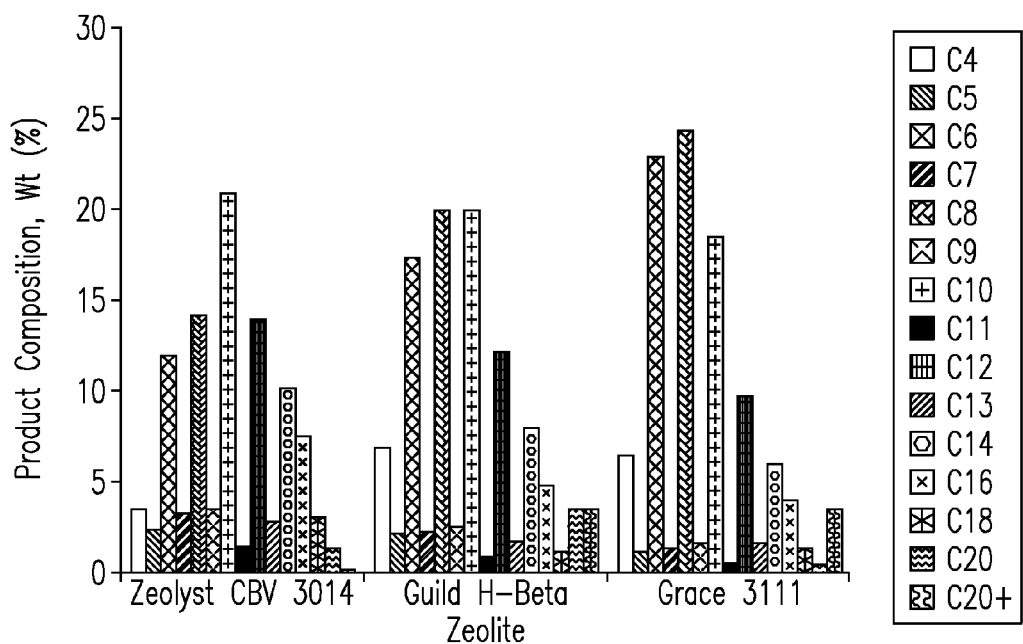

FIG. 11 shows simulated distillation profiles for products generated at each reactor temperature, along with reference standards for kerosene and diesel fuel. Simulated yields of C8+ and C10+ compounds are reported assuming 98% conversion of ethylene from the ethylene oligomerization described in EXAMPLE 12. FIG. 12 compares product composition at 250° C. with those obtained with other catalysts at the same temperature.

Example 15

Second Oligomerization, Test 3

0.50 g of CBV 3104 catalyst of a (−80/+100) mesh (Zeolyst International, Malvern, Pa., USA) was calcined at 550° C. for 4 hrs in air and loaded and tested with an identical feed and in a similar manner as described in EXAMPLE 14. TABLE 2 lists compositions of liquid product samples obtained at various reactor temperatures.

TABLE 2 compares compositions of liquid product samples obtained at various reactor temperatures for second oligomerization tests with CBV 3104 catalyst.

| Composition by Carbon No. | Reactor Temperature, ° C. | | | |
|---|---|---|---|---|
| | 200 | 250 | 300 | 350 |
| C4 | 5% | 3% | 2% | 4% |
| C5 | 1% | 2% | 5% | 6% |
| C6 | 15% | 12% | 9% | 10% |
| C7 | 1% | 3% | 8% | 9% |
| C8 | 17% | 14% | 13% | 13% |
| C9 | 1% | 4% | 8% | 8% |
| C10 | 22% | 21% | 18% | 19% |
| C11 | 1% | 1% | 3% | 3% |
| C12 | 16% | 14% | 14% | 12% |
| C13 | 2% | 3% | 3% | 3% |
| C14 | 10% | 10% | 10% | 8% |
| C16 | 7% | 7% | 6% | 4% |
| C18 | 2% | 3% | 2% | 1% |
| C20+ | 1% | 1% | | |
| Yield C8+ | 77% | 77% | 74% | 69% |
| Yield C10+ | 59% | 60% | 54% | 48% |

FIG. 12 compares the product composition at 250° C. with those obtained with other catalysts at the same temperature.

Example 16

Second Oligomerization, Test 4

0.50 g of W.R. Grace & Co. Davicat 3111 (−35/+100) mesh which had been calcined at 400° C. for 2 hrs in air was loaded and tested in manner similar to the method disclosed in EXAMPLE 14. Liquid produced during a portion of the test described in EXAMPLE 12 was fed to the reactor at 0.05 mL/min. TABLE 3 lists compositions of samples taken from the liquid product at various reactor temperatures.

TABLE 3 lists compositions of samples taken from the liquid product obtained at various second oligomerization reactor temperatures using Grace 3111 as catalyst.

| Composition | Reactor Temperature, ° C. | | | |
|---|---|---|---|---|
| | 200 | 250 | 300 | 350 |
| C4 | 7% | 12% | 6% | 7% |
| C5 | 2% | 2% | 3% | 3% |
| C6 | 14% | 23% | 18% | 23% |
| C7 | 2% | 2% | 3% | 3% |
| C8 | 17% | 20% | 22% | 26% |
| C9 | 3% | 2% | 3% | 2% |
| C10 | 19% | 17% | 19% | 18% |
| C11 | 1% | 1% | 1% | 1% |
| C12 | 13% | 10% | 11% | 9% |
| C13 | 1% | 1% | 2% | 1% |
| C14 | 10% | 6% | 7% | 4% |
| C16 | 7% | 3% | 4% | 2% |
| C18 | 3% | 1% | 1% | |
| C20+ | | | | |
| Yield C8+ | 73 | 60 | 68 | 63 |
| Yield C10+ | 53 | 38 | 44 | 35 |

FIG. 12 compares product composition at 250° C. with those obtained with other catalysts at the same temperature.

Example 17

50:50 Recycle of First and Second Oligomerization Products

Figure 13:
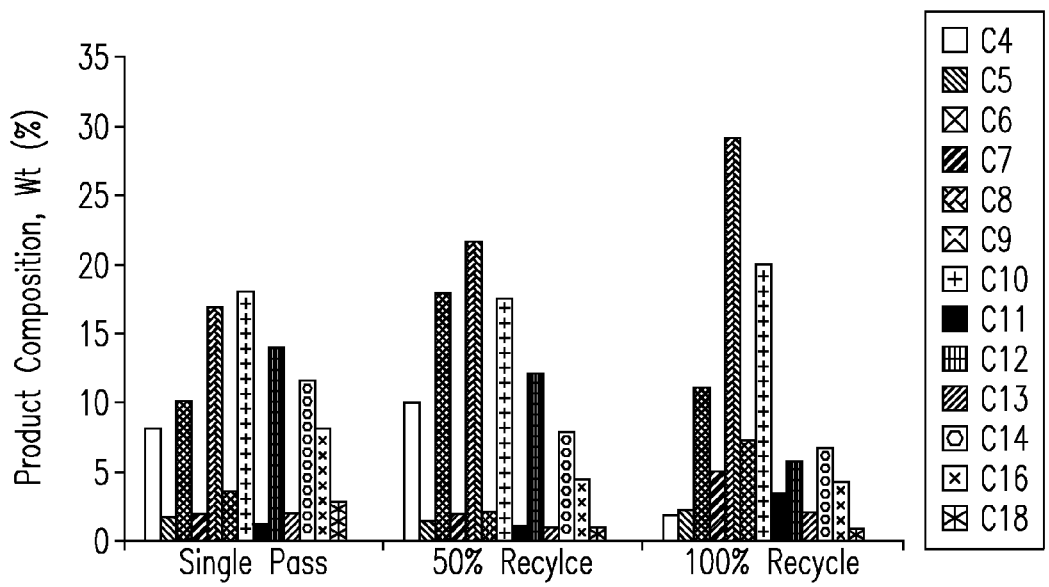

EXAMPLE 17 demonstrates recycling of second oligomerization light products back through the second oligomerization reactor and process to increase molecular weight to form fuel-range hydrocarbons. One part by weight of a second oligomerization distillate fraction containing light hydrocarbons boiling at a temperature less than 136.8° C. (obtained by distillation of a second oligomerization product) was mixed with one part by weight of a composite sample taken from a typical first oligomerization product to produce a 50:50 mixture that was used as a feed to the second oligomerization reactor. Testing and product analyses were performed as described in EXAMPLE 13. 1.63 g of W.R. Grace & Co. Davicat SiAl 3111 (−60/+100 mesh) was loaded into the flow reactor for the recycle testing. Reactor bed temperature was held at 225° C. and a pressure of 300 psig. Product obtained at a feed rate of 0.10 mL/min contained compounds with carbon numbers ≥C8 of 68% and ≥C10 of 45% comparable to the product obtained in EXAMPLE 15 (100% first oligomerization product feed, i.e., no recycle). FIG. 13 compares product composition for 50% recycle at 225° C. with products from comparable experiments performed at the same temperature with no recycle stage (i.e., single pass first oligomerization product as a feed) and with a feed consisting of 100% recycled second oligomerization lights described in EXAMPLE 18. Product compositions are similar for these recycle experiments.

The 50% recycle experiment was continued by first regenerating the catalyst at 550° C. for 4 h in air, after which the liquid feed rate was decreased to 0.075 mL/min to determine the effect of feed rate. Results show that decreasing the feed rate shifted the composition toward a higher carbon number. At a flow rate of 0.075 mL/min, composition showed compounds were obtained with a carbon numbers ≥C8 of 79% and ≥C10 of 57%.

Example 18

Recycle of Light Olefins from Second Oligomerization Back to Second Oligomerization Stage or Process A feed consisting of 100% distilled lights from second oligomerization products boiling at a temperature less than 150° C. were passed over a catalyst bed comprised of 1.57 g of Grace Davicat SIAL 3111 at a flow rate of 0.066 mL/min, at a temperature of 225° C. and a reactor pressure of 300 psig. Product obtained contained compounds with a carbon number ≥C8 of 80% and ≥C10 of 44%. FIG. 13 compares product composition at 225° C. with comparable experiments performed at the same temperature and varying degrees of recycle. Light olefin products from the second oligomerization stage or process can be recycled without dilution back to the second oligomerization reactor for conversion to fuel-range products, increasing the overall yield after a single recycle to ≥C8 of about 90% and ≥C10 of about 70%.

Example 19

Integration of Ethanol Dehydration with First Oligomerization Stage or Process

EXAMPLE 19 demonstrates the integration of an ethanol dehydration process with the first oligomerization stage or process. Ethanol (96 wt % in water) was fed to a ⅜" OD stainless steel tube reactor loaded with 1.10 g of W.R. Grace & Co. Davicat SIAL 3111 catalyst. Catalyst was calcined at 500° C. for 4 hrs and sized to −60/+100 mesh prior to loading. Ethanol was fed to the reactor at a rate of 0.1 mL/min at 360° C. and a pressure of 300 psig. $N_2$ was used as a carrier gas that was co-fed to the reactor at a rate of 12.4 cm$^3$/min. Ethanol conversion was between 90% and 95%. Ethylene yield was 55% to 67% on average. Gaseous effluent from the reactor was passed through silica gel and activated carbon filters prior to entering the molecular sieve and Cu scrubbers. Ethylene-rich reactor effluent then passed over the catalyst disclosed in EXAMPLE 3 at 85° C. and 300 psig. Other parameters for this reactor were similar to the process disclosed in EXAMPLE 9. Ethylene conversion of 98-100% was observed. The liquid product consisted of 65% C4, 21% C6, 9% C8, 5% C10 and 1% C12.

Example 20

Olefin Metathesis

EXAMPLE 20 demonstrates results from exemplary olefin metathesis of a composite mixture containing a 50:50 mixture of a first oligomerization test product and a second oligomerization test product that were reacted with ethylene. 1.7 g of the catalyst prepared in EXAMPLE 8 was loaded into a ⅜" stainless steel tube reactor. Reactor temperature was 120° C. Reactor pressure was held at 300 psig. The liquid feed was introduced to the reactor at a rate of 0.044 mL/min. Ethylene was fed to the reactor at a rate of 29 cm$^3$/min. TABLE 4 discloses the relative concentration of the liquid reactor products as grouped by carbon number. The gas phase product contained 6% propene.

TABLE 4 lists relative concentrations of liquid reactor products from olefin metathesis testing grouped by carbon number.

| Composition | Liquid Feed | Liquid Product |
|---|---|---|
| C4 | 58 | 59 |
| C5 |  | 14 |
| C6 | 26 | 19 |
| C7 |  | 2 |
| C8 | 11 | 4 |
| C9 |  |  |
| C10 | 5 | 1 |
| C11 |  |  |
| C12 | 1 |  |
| C13 |  |  |
| C14 |  |  |
| C16 |  |  |
| C18 |  |  |

Example 21

One Step Process 25.28 g of Zeolyst CBV3020 CY 1.6 (Si/Al$_2$ ratio: 30) catalyst was loaded into a 60 cm$^3$ stainless steel tube for reaction testing. The reactor was operated over several days at a temperature between 270° C. and 350° C. and a pressure between 150 psig and 500 psig. Ethanol flow to the reactor was varied from 0.20 to 1.00 mL/min. Ethanol concentration varied from 85% ethanol in water to 100% ethanol. A $N_2$ carrier gas also passed through the reactor at 25-50 cm$^3$/min. About 2 L of material were produced during several days of testing. At 340° C. using 85% ethanol in water and a liquid feed flow rate of 1.00 mL/min, the hydrocarbon yield was 63.29% on a gram liquid hydrocarbon produced per gram of ethylene fed basis. (Ethanol was fed to the reactor but yield was calculated on the ethylene weight basis.) At 350° C., 350 psig and 0.2 mL/min, the hydrocarbon yield was 44.9-46.3% over 3 days. The liquid samples produced were composited into a single sample with a carbon number composition of ≥C8 of 85.2% and ≥C10 of 61.9%. The aromatic content of this composite can be estimated to be 75% to 85% as indicated by the cycloparaffin content of the hydrotreated product, discussed in EXAMPLE 30.

Example 22

One Step Process, Test 2

EXAMPLE 21 was repeated except that 31.1 g of Zeolyst CBV 28014 CY 1.6 (Si/Al$_2$=280) catalyst was used. The reactor was operated over a period of several days. Temperature was selected between 340° C. and 360° C. Reactor pressure was 150 psig. Ethanol flow to the reactor was varied from 0.10 to 0.30 mL/min. Ethanol concentration was 92.5% ethanol in water. A $N_2$ carrier gas also passed through the reactor at 50 cm$^3$/min. Liquid products were composited to a single sample with a carbon number composition of ≥C8 of 77.5% and ≥C10 of 48.1%.

Example 23

Alkylation

Figure 14:
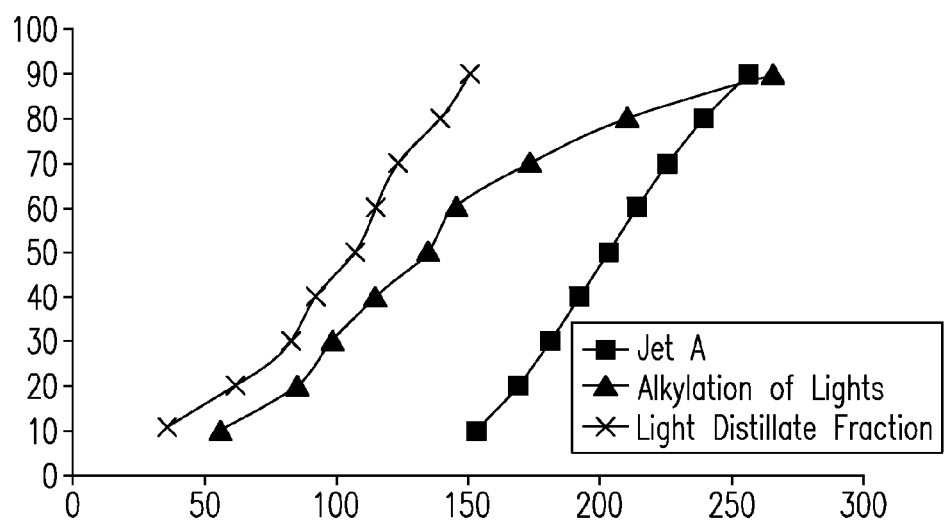

EXAMPLE 23 demonstrates alkylation of one-step light products with ethylene to increase yield of fuel-range hydrocarbons. A portion of the composited hydrocarbon produced in EXAMPLE 22 was fractionated by distillation up to a temperature of 115° C. to collect a quantity of light hydrocarbons. 8.3 g of the light hydrocarbons were added to 0.45 g H-ZSM-5 catalyst (Zeolyst CBV 28014 powder calcined 500° C., 4 hr in air) in a steel autoclave vessel. The vessel was sealed and ethylene was charged to 100 psig at room temperature. The mixture was heated (while stirring) to 250° C. internal temperature and continued overnight. Mass of the hydrocarbon mixture increased by 0.81 g. FIG. 14 shows simulated distillation curves of the feed (light distillate fraction) and alkylated product (alkylation of lights). The feed had a composition with a carbon number distribution of ≥C8 of 55.5% and ≥C10 of 10.4%. The alkylated product had a greater fraction in the distillate fuel range with a composition with a carbon number distribution of ≥8 of 60.3% and ≥C10 of 15.4%.

Example 24

Alkylation

A product produced by the method of EXAMPLE 21 was fractionated until the vapor temperature of the distilling lights increased to 125° C. The fraction that distilled up to 125° C. was alkylated with ethylene. 2.83 g of BASF Beta 35 zeolite (L7134-47-2) was added to 80.65 g of the distilled fraction in a stainless steel autoclave vessel. The autoclave was sealed and heated to 250° C. Ethylene was added such that the total pressure was 2400 psig at temperature. After 14 hrs, the pressure had decreased to 2000 psig. The feed had a composition with a carbon number distribution of ≥C8 of 48.5% and ≥C10 of 11.0%. The alkylated product had a greater fraction in the distillate fuel range with a composition with a carbon number distribution of ≥C8 of 71.3% and ≥C10 of 43.0%.

Example 25

Alkylation of a Mixture Containing a One-Step Product and a Two-Step Oligomerization Product EXAMPLE 25 demonstrates alkylation of a one-step product with a two-step first oligomerization product. 53.0 g of the fraction of a one-step product prepared by the method of EXAMPLE 21 distilling between 115 and 135° C. was mixed with 43.0 g of first oligomerization product produced by the method of EXAMPLE 9, except using the catalyst of EXAMPLE 1. The hydrocarbon mixture was fed at 0.1 mL/min (WHSV=4) with 6 mL/min of $N_2$ carrier gas over a Beta zeolite catalyst (Zeolyst CP814C; Si/Al ratio=38) at 250° C. Reactor pressure was 500 psig. Results show the alkylation increased the carbon number in the product. Composition of the feed included a carbon number distribution of ≥C8 of 74% and ≥C10 of 4%. Composition of the product included a carbon number distribution of ≥C8 of 89% and ≥C10 of 33%.

Example 26

Hydrotreatment of a One-Step Product

Figure 15:
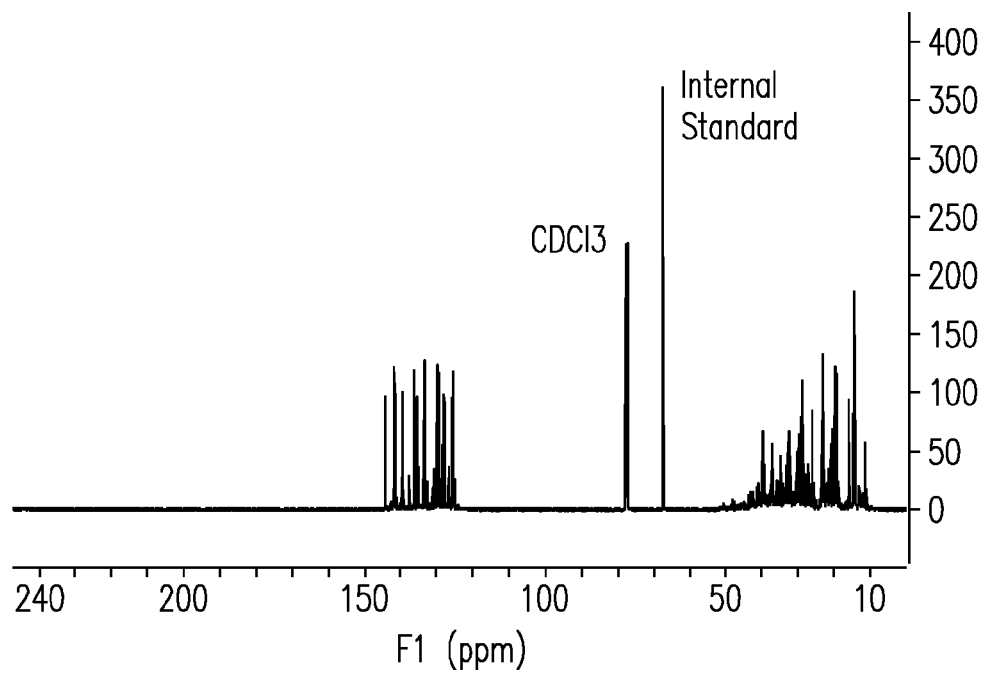

EXAMPLE 21 was repeated except that 1.00 g of Zeolyst CBV3024 CY 1.6 (Si/Al$_2$=80) catalyst was used in a ⅜" OD stainless steel reactor. Over the course of several days, the reactor was operated at 360° C. and 230 psig. Ethanol flow to the reactor was varied from 0.08-0.15 mL/min. Ethanol concentration was 53% ethanol in water. A $N_2$ carrier gas was also passed through the reactor at 25 cm³/min. The combined product was fractionated to collect the material distilling above 140° C. A portion of this material (173.61 g) was placed in a steel autoclave and 12.12 g of 2% Pt on ⅛" $Al_2O_3$ pellets from Engelhard was added. The autoclave was sealed, pressurized with $H_2$ and heated to 200° C. for one day. The pressure was maintained at 400 psig by periodic additions of $H_2$. FIG. 15 shows the NMR spectrum of the product. Results demonstrate that use of these conditions for light hydrotreating of one-step products does not reduce aromatic groups to cyclic paraffins under the selected reaction conditions over the Pt catalyst. By integration of the NMR spectrum, 23.5% of the carbon in this lightly hydrotreated material is in an aromatic ring.

Example 27

Hydrotreatment of a Two-Step Product

Figure 16:
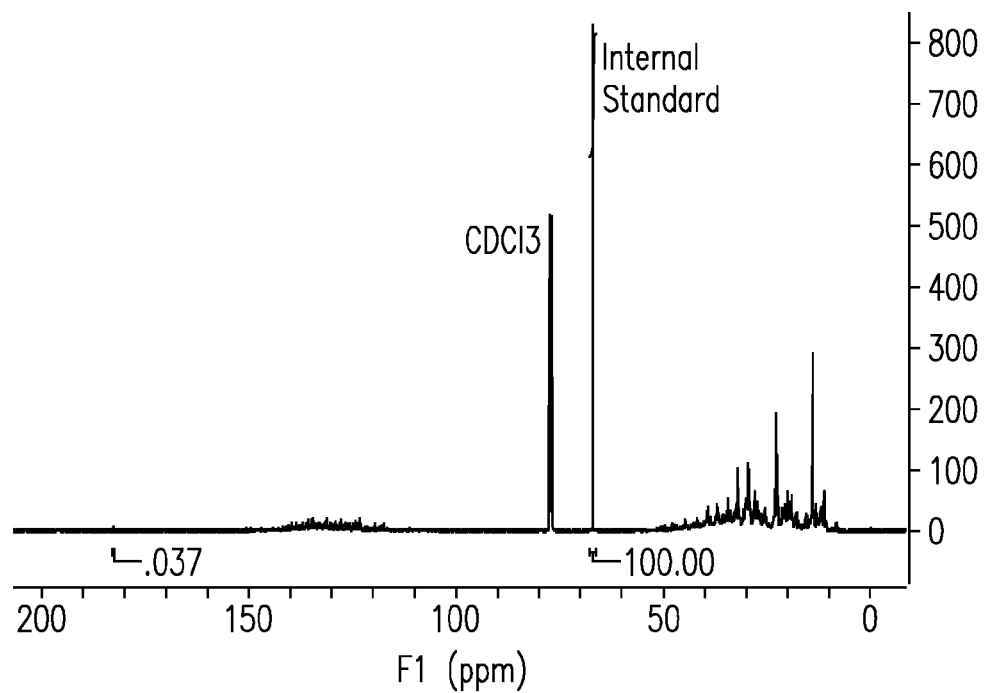
Figure 17:
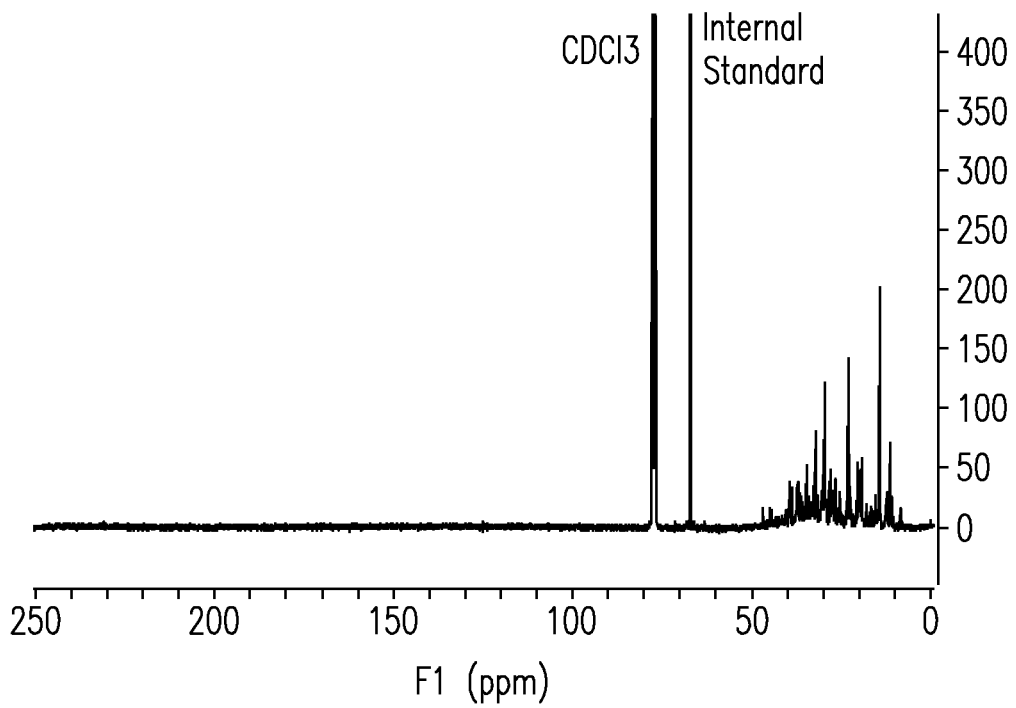
Figure 18:
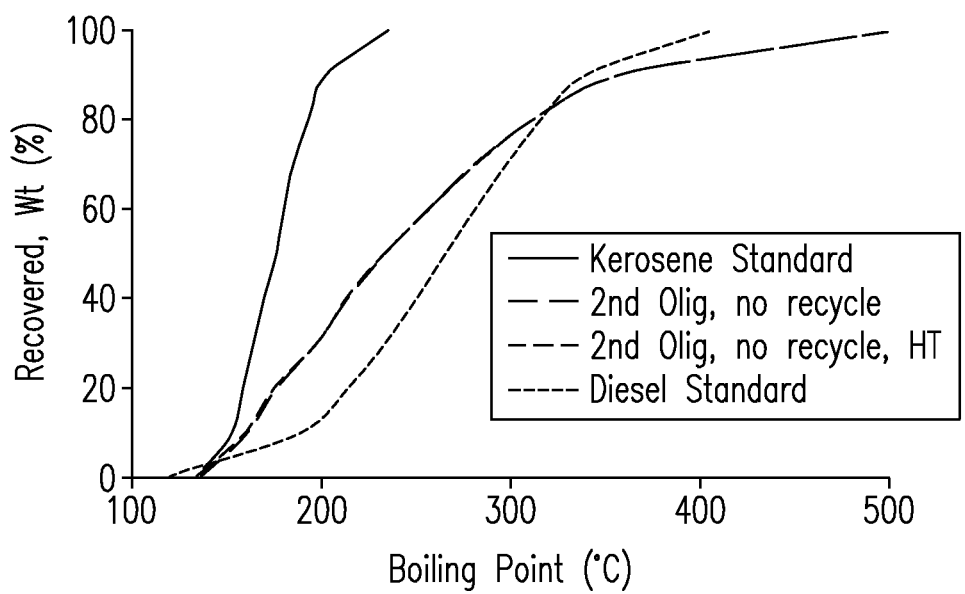

EXAMPLE 27 demonstrates light hydrotreating of two-step products to distillate fuel-range hydrocarbons under selected conditions, in which aromatics were shown not to be reduced. In a steel autoclave, 12.12 g of 2% Pt on ⅛" $Al_2O_3$ pellets from Engelhard was added to 327 g of the fraction of the second oligomerization product from EXAMPLE 16 produced at 225° C. that distills above 150° C. FIG. 16 shows the NMR spectrum of the olefin feed. The spectrum shows the presence of highly branched olefins at a level consistent with about one olefin group per molecule. The autoclave was sealed, pressurized with $H_2$ and heated to 200° C. Pressure was maintained at 425 psig by periodic additions of $H_2$. The hydrogenation reaction continued overnight. FIG. 17 presents NMR analysis results for the hydrotreated product hydrotreated under conditions that do not reduce aromatics. Results show that no aromatic or olefinic carbons are present in the product and that the hydrotreating conditions are sufficient to reduce the olefins to iso-paraffins. FIG. 18 presents simulated distillation (simdist) results. Data show that most of the hydrotreated product is in the jet fuel range. Data in the figure also show that simdist results of olefin feeds are identical to those for the hydrotreated materials.

Example 28

Fractionation and Hydrotreatment of a Two-Step Product to a Jet Fuel

EXAMPLE 28 demonstrates hydrotreating of two-step products to distillate fuel-range hydrocarbons under selective conditions of EXAMPLE 26, in which aromatics were shown not to be reduced. In a steel autoclave, 12.12 g of 2% Pt on ⅛" $Al_2O_3$ pellets from Engelhard was reused from EXAMPLE 26 to reduce composites of the fraction of the second oligomerization product prepared by the method of EXAMPLE 16 produced at 225° C. that distills above about 140° C. Several batches were reduced in order to collect about 1.5 L of lightly hydrotreated product. The autoclave was sealed, pressurized with $H_2$ to between 400 and 500 psig and heated to 200° C. Each hydrogenation reaction continued overnight. Hydrotreated materials were composited and fractionally distilled. The fraction distilling from about 150 to about 270° C. comprising about 1 L was submitted to the Air Force Research Laboratory (AFRL) for testing under guidelines of ASTM D4054, "*Standard Practice for the qualification and Approval of new Aviation Turbine Fuels* and Fuels Additives." The testing was to determine the suitability of the material as an alternative aviation fuel that could satisfy the specification requirements outlined in D7566-12A. TABLE 5 lists results of GC×GC testing.

TABLE 5 lists results from GC × GC testing of two-step product from EXAMPLE 28 conducted by AFRL.

| Component | Weight % | Volume % |
|---|---|---|
| Total Alkylbenzenes | 0.98 | 0.78 |
| Total Alkylnaphthalenes | <0.01 | <0.01 |
| Total Cycloaromatics | 0.60 | 0.49 |
| Total iso-Paraffins | 96.84 | 97.19 |
| Total n-Paraffins | 0.79 | 0.82 |
| Total Monocycloparaffins | 0.75 | 0.70 |
| Total Dicycloparaffins | 0.03 | 0.03 |
| Total Tricycloparaffins | <0.01 | <0.01 |

Results confirm the low aromatic content and the very high isoparaffin compound content. TABLE 6 compares product properties for a test sample against ASTM specifications for two aviation jet fuels.

TABLE 6 compares product properties for a hydrotreated and fractionated two-step product against ASTM specifications for two aviation jet fuels.

| Method | Test | D7566 | Jet A-1 | Result |
|---|---|---|---|---|
| ASTM D 86 | Distillation: | | | |
| | Initial Boiling Point (° C.) | | | 164 |
| | 10% Recovered (° C.) | <205 | <205 | 177 |
| | 20% Recovered (° C.) | | | 182 |
| | 50% Recovered (° C.) | | | 205 |
| | 90% Recovered (° C.) | | | 254 |
| | Endpoint (° C.) | <300 | <300 | 272 |
| | Residue (% vol) | | <1.5 | 1.6 |
| | Loss (% vol) | | <1.5 | 0.7 |
| | T90-T10 | >22 | >40 | 77 |
| | T50-T10 | | >15 | 28 |
| ASTM D 93 | Flash Point (° C.) | 38 | 38 | 52 |
| ASTM D 3241 | Thermal Stability JFTOT @325 (° C.) | 325 | 260 | |
| | Tube Deposit Rating (Visual) | <3 | <3 | 1 |
| | Change in Pressure (mm Hg) | <25 | <25 | 0 |
| ASTM D 4809 | Net Heat of Combustion (MJ/kg) | | >42.8 | 43.7 |
| ASTM D 7171 | Hydrogen Content by NMR (% mass) | | | 15.2 |
| ASTM D 5972 | Freeze Point (° C.) | <−40 | <−47 | <−70 |
| ASTM D 4052 | Density (kg/L, 15° C.) | 0.730 to 0.770 | 0.775 to 0.840 | 0.775 |

Example 29

Figure 19:
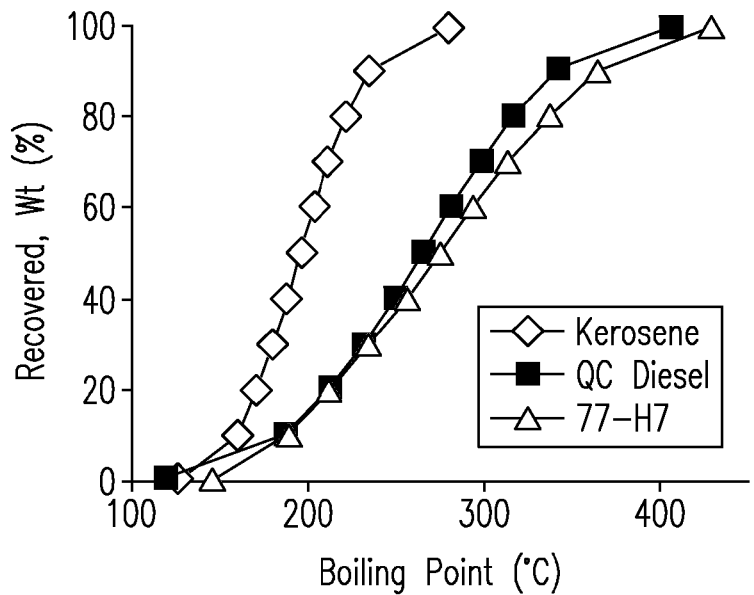

Preparation of a Two-Step Product, Hydrotreatment, and Fractionation to Diesel and Gasoline Fuels EXAMPLE 29 demonstrates the conversion of first oligomerization products to fuel-range hydrocarbons in a second oligomerization reactor, hydrotreatment and fractionation to a diesel range alternate fuel. H-Beta zeolite (e.g., −12 to +30 mesh zeolite, Guild Associates, Dublin, Ohio, USA) was calcined ex-situ in air at a temperature of 550° C. for 3 hr. 13.9 g of the calcined zeolite was loaded into a tube reactor. First oligomerization product was introduced to the reactor at a rate of 1.4033 mL/min. A carrier gas of nitrogen ($N_2$) was fed to the reactor at a flow rate of about 10 $cm^3$/min. The reactor was maintained at a nominal pressure of 300 psig and a temperature of 225° C. Liquid product was collected at system pressure in condensers chilled to a temperature of 10° C. Second oligomerization product was lightly hydrotreated using the method of EXAMPLE 27. The hydrotreated material was distilled and the fraction boiling between about 160 and about 390° C. was collected. Simulated distillation of this fraction shown in FIG. 19 demonstrates the material had distillation properties nearly identical to a standard diesel fuel. The material had a pour point of −66.0° C., a cloud point of −60.1° C., and a derived cetane value of 53.6. The light fraction boiling below 160° C. was a gasoline fraction with an octane number of 83.

Example 30

Fractionation and Hydrotreatment of a One-Step Product to a Fuel Blend

A portion of the composite of one-step hydrocarbon products obtained in EXAMPLE 21 was hydrotreated over 406 g of a Engelhard Ni 0750 catalyst (Iselin, N.J.) in a fixed bed reactor. Hydrogenation was conducted under mild, medium, and heavy treatment conditions as described in TABLE 7. The key properties of density and freeze point for each set of conditions are shown demonstrating that at least a medium treatment is effective at attaining freeze points lower than the target −47° C. A composite of the hydrogenated product was fractionated and the fraction boiling between about 150° C. and about 200° C. was collected and designated H2-1. A second portion of the hydrogenated product was also fractionated and the fraction boiling between about 150° C. and about 230° C. was collected and designated H2-2. Samples were submitted to the Air Force Research Laboratory (AFRL) for testing under guidelines of ASTM D4054, "*Standard Practice for the qualification and Approval of new Aviation Turbine Fuels and Fuels Additives.*" Testing determined suitability of the material as an alternative aviation fuel that could satisfy the specification requirements outlined in D7566-12A. TABLE 8 lists results of GC×GC testing.

TABLE 7 lists nominal processing conditions and properties of hydrotreated one-step products.

| Sample | Temperature, ° C. | Pressure, psig | LHSV, $h^{-1}$ | Freeze Point, ° C. | Density, kg/L |
|---|---|---|---|---|---|
| Feed | — | — | — | −14.3 | |
| Heavy Treatment | 200 | 1000 | 0.5 | −73 | 0.788 |

TABLE 7-continued lists nominal processing conditions and properties of hydrotreated one-step products.

| Sample | Temperature, ° C. | Pressure, psig | LHSV, h$^{-1}$ | Freeze Point, ° C. | Density, kg/L |
|---|---|---|---|---|---|
| Medium Treatment | 180 | 700 | 0.5 | −52 | 0.793 |
| Mild Treatment | 160 | 450 | 0.625 | −37 | 0.799 |

TABLE 8 lists results from GC × GC testing of one-step products from EXAMPLE 30 conducted by AFRL.

| GC × GC (mass %) | 7933 H2-1 | 7934 H2-2 | 4909 F-T SPK | 4751 JP-8 |
|---|---|---|---|---|
| n-Paraffins | 0.3 | 0.2 | 19.1 | 18.8 |
| iso-Paraffins | 5.7 | 5.8 | 79.5 | 31.4 |
| Monocyclopafaffins | 85.5 | 74.5 | 12 | 20.8 |
| Dicycloparaffins | 6.0 | 16.2 | <0.1 | 5.7 |
| Alkylbenzenes | 2.4 | 2.9 | 0.2 | 15.1 |
| Indans and Tetralins | 0.1 | 0.4 | 0.1 | 6.5 |
| Naphthalene | <0.1 | <0.1 | <0.1 | 0.1 |
| Naphthalenes | <0.1 | <0.1 | <0.1 | 1.6 |
| Total | 100 | 100 | 100 | 100 |

Results confirm the high cyclic paraffin content, which arises from hydrotreatment of the highly aromatic one-step reactor product. TABLE 9 compares product properties for a test sample against ASTM specifications for two aviation jet fuels.

TABLE 9 compares product properties for hydrotreated and fractionated one-step products against ASTM specifications for two aviation jet fuels.

| Specification Test | MIL-DTL-83133H Spec Requirement | 7933 H2-1* | 7934 H2-2* | 4909 FT-SPK* | 4751 JP-8* |
|---|---|---|---|---|---|
| Aromatics, vol % | ≤25 | 1.9 | 2.2 | 0.0 | 18.8 |
| Olefins, vol % |  | 1.2 | 1.1 | 0.0 | 0.8 |
| Heat of Combustion (measured), MJ/Kg | ≥42.8 | 43.1 | 43.1 | 44.3 | 43.3 |
| Distillation: |  |  |  |  |  |
| IBP, ° C. |  | 161 | 165 | 144 | 159 |
| 10% recovered, ° C. | ≤205 | 165 | 171 | 167 | 182 |
| 20% recovered, ° C. |  | 166 | 173 | 177 | 189 |
| 50% recovered, ° C. |  | 171 | 183 | 206 | 208 |
| 90% recovered, ° C. |  | 190 | 220 | 256 | 244 |
| EP, ° C. | ≤300 | 214 | 243 | 275 | 265 |
| T90-T10, ° C. | 22 | 25 | 49 | 89 | 62 |
| Residue, % vol | ≤1.5 | 1.1 | 1.1 | 1.5 | 1.3 |
| Loss, % vol | ≤1.5 | 1 | 0.8 | 0.9 | 0.8 |
| Flash point, ° C. | ≥38 | 44 | 48 | 45 | 51 |
| Freeze Point, ° C. | ≤−47 | <−60 | <−60 | −51 | −50 |
| Density@15° C., kg/L | 0.775-0.840 (0.751-0.770) | 0.803 | 0.814 | 0.756 | 0.804 |

Figure 20:
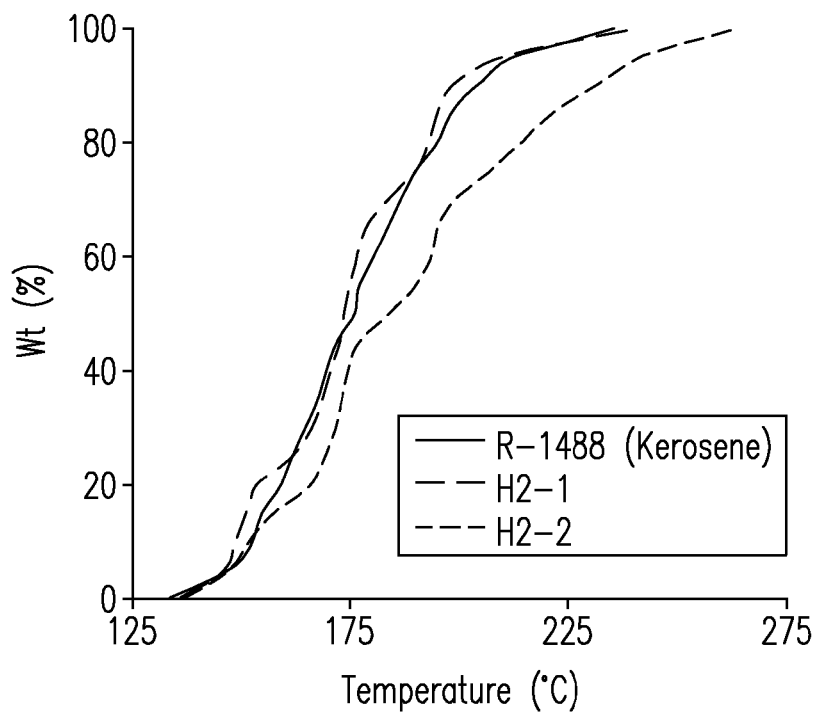

FIG. 20 presents simulated distillation (simdist) results for the H2-1 and H2-2 products. Data show that the H2-1 product has a distillation profile nearly identical to a standard kerosene. H2-2 is heavier and closely resembles a jet fuel or jet blend stock.

While exemplary embodiments of the present invention have been shown and described, it will be apparent to those skilled in the art that many changes and modifications may be made without departing from the invention in its true scope and broader aspects. The appended claims are therefore intended to cover all such changes and modifications as fall within the scope of the present invention.

What is claimed is:

1. A process for converting feedstocks to distillate-range hydrocarbon fuels, comprising:
   oligomerizing an ethylene-containing feed over a first catalyst at a temperature selected from about 40° C. to about 220° C. to form a water-free first oligomerization product in a first reaction stage, wherein the water-free first oligomerization product contains a majority concentration of mixed olefins with a carbon number from about C4 to about C8;
   oligomerizing the mixed olefins in the water-free first oligomerization product over a second catalyst at a temperature from about 150° C. to about 350° C. to form a two-step oligomerization product at a yield greater than or equal to about 20% containing mixed open-chain linear and branched olefins with a carbon number from about C8 to about C23; and
   combining together selected portions of (a) the two-step oligomerization product and a first hydrocarbon product or (b) the two-step oligomerization product, the first hydrocarbon products, and a second hydrocarbon product to form a blend comprising any selected ratio of open-chain and closed-chain hydrocarbons;
   wherein the first hydrocarbon product is derived from an ethanol-containing feed and comprises a majority concentration of mixed cycloparaffin hydrocarbons and mixed closed-chain aromatic hydrocarbons with a carbon number between about C3 to about C12; and the second hydrocarbon product comprises a selected quantity of alkylated aromatic hydrocarbons.

2. The process of claim 1, further including mixing the water-free first oligomerization product with the first hydrocarbon product to make a feed, and alkylating the feed over an alkylation catalyst to form the second hydrocarbon product comprising alkylated aromatic hydrocarbons.

3. The process of claim 2, wherein the second hydrocarbon product contains more hydrocarbons with carbon numbers greater than C8 than the feed.

4. The process of claim 2, wherein the second hydrocarbon product contains more hydrocarbons with carbon numbers greater than C10 than the feed.

5. The process of claim 1, further including hydrotreating the blend to yield a majority of fuel range hydrocarbons boiling in the range of temperatures from about 120° C. to about 390° C.

6. The process of claim 1, further including hydrotreating each of the first hydrocarbon product, the second hydrocarbon product, and/or the two-step oligomerization product prior to combining the selected portions together to yield a majority of fuel range hydrocarbons boiling in the range of temperatures from about 120° C. to about 390° C.

7. The process of claim 1, further including optionally fractionating the two-step oligomerization product at a selected fractionation temperature to obtain individual fractions, a fraction containing distillate-range olefins boiling at or higher than the fractionation temperature and a light fraction boiling at or below the fractionation temperature.

8. The process of claim 7, wherein the fractionation temperature is selected in the range from about 100° C. to about 140° C.

9. The process of claim 7, wherein the fractionation temperature is selected in the range from about 140° C. to about 180° C.

10. The process of claim 7, further including hydrogenating the distillate-range olefins to form a mixture of open-chain hydrocarbons including linear and branched open-chain paraffins.

11. The process of claim 10, wherein a majority of open-chain hydrocarbons in the mixture are in the jet fuel range.

12. The process of claim 10, wherein a majority of open-chain hydrocarbons in the mixture are in the diesel fuel range.

13. The process of claim 7, further including mixing the light fraction with the first hydrocarbon product containing aromatic hydrocarbons to make a feed, and alkylating the feed over an alkylation catalyst to form the second hydrocarbon product comprising alkylated aromatic hydrocarbons.

14. The process of claim 13, wherein the second hydrocarbon product contains more hydrocarbons with carbon numbers greater than C8 than the feed.

15. The process of claim 13, wherein the second hydrocarbon product contains more hydrocarbons with carbon numbers greater than C10 than the feed.

16. The process of claim 1, further including mixing ethylene or an ethylene-containing feed with the first hydrocarbon product containing aromatic hydrocarbons to make a feed, and alkylating the feed over an alkylation catalyst to form the second hydrocarbon product comprising alkylated aromatic hydrocarbons.

17. The process of claim 16, wherein the second hydrocarbon product contains more hydrocarbons with carbon numbers greater than C8 than the feed.

18. The process of claim 16, wherein the second hydrocarbon product contains more hydrocarbons with carbon numbers greater than C10 than the feed.

19. The process of claim 1, further including combining selected ratios of the first hydrocarbon product containing aromatic hydrocarbons and the second hydrocarbon product containing alkylated aromatic hydrocarbons to make a feed and hydrogenating the feed to obtain a mixture of closed-chain hydrocarbons including closed-chain aromatics and closed-chain paraffins.

20. The process of claim 19, wherein the hydrogenation includes converting from 0% to about 33% of the closed-chain aromatics to closed-chain paraffins.

21. The process of claim 19, wherein the hydrogenation includes converting from about 33% to about 66% of the closed-chain aromatics to closed-chain paraffins.

22. The process of claim 19, wherein the hydrogenation includes converting from about 66% to about 100% of the closed-chain aromatics to closed-chain paraffins.

23. The process of claim 19, further including combining a selected ratio of the mixture containing closed-chain hydrocarbons and a mixture containing open-chain hydrocarbons including linear and branched open-chain paraffins to make a fuel blend, wherein the mixture containing open-chain hydrocarbons is obtained from a fraction derived from fractionation of the two-step oligomerization product containing distillate-range olefins boiling at or higher than the fractionation temperature that is further hydrogenated.

24. The process of claim 23, further including fractionating the fuel blend to obtain individual fractions, a fraction containing distillate-range hydrocarbons boiling in the range of temperatures from about 120° C. to about 300° C., a light fraction boiling below a temperature of about 120° C., and a heavy fraction boiling above a temperature of about 300° C.

25. The process of claim 24, wherein the distillate-range hydrocarbons are in the jet fuel range.

26. The process of claim 24, wherein the light fraction contains hydrocarbons in the gasoline fuel range.

27. The process of claim 23, further including fractionating the fuel blend to obtain individual fractions, a fraction containing distillate-range hydrocarbons boiling in the range of temperatures from about 160° C. to about 390° C., a light fraction boiling below a temperature of about 160° C., and a heavy fraction boiling above a temperature of about 390° C.

28. The process of claim 27, wherein the distillate-range hydrocarbons are in the diesel fuel range.

29. The process of claim 27, wherein the light fraction contains hydrocarbons in the gasoline fuel range.

30. The process of claim 1, further including combining a selected ratio of the first hydrocarbon product containing aromatic hydrocarbons, the second hydrocarbon product containing alkylated aromatic hydrocarbons and a fraction containing distillate-range olefins to make a fuel blend, wherein the fraction containing distillate-range olefins is obtained from fractionation of the two-step oligomerization product containing distillate-range olefins boiling at or higher than the fractionation temperature.

31. The process of claim 30, wherein the fuel blend includes up to 33% distillate-range olefins.

32. The process of claim 30, wherein the fuel blend includes up to 66% distillate-range olefins.

33. The process of claim 30, wherein the fuel blend includes up to 100% distillate-range olefins.

34. The process of claim 30, further including hydrogenating the fuel blend to obtain a hydrogenated blend comprising a mixture of closed-chain aromatics, closed-chain paraffins, open-chain paraffins, and open-chain iso-paraffins.

35. The process of claim 34, wherein the hydrogenation includes converting from 0% to about 33% of the closed-chain aromatics to closed-chain paraffins.

36. The process of claim 34, wherein the hydrogenation includes converting from about 33% to about 66% of the closed-chain aromatics to closed-chain paraffins.

37. The process of claim 34, wherein the hydrogenation includes converting from about 66% to about 100% of the closed-chain aromatics to closed-chain paraffins.

38. The process of claim 34, further including fractionating the fuel blend to obtain individual fractions, a fraction containing distillate-range hydrocarbons boiling in the range of temperatures from about 120° C. to about 300° C., a light fraction boiling below a temperature of about 120° C., and a heavy fraction boiling above a temperature of about 300° C.

39. The process of claim 38, wherein the distillate-range hydrocarbons are in the jet fuel range.

40. The process of claim 38, wherein the light fraction contains hydrocarbons in the gasoline fuel range.

41. The process of claim 34, further including fractionating the hydrogenated blend to obtain individual fractions, a fraction containing distillate-range hydrocarbons boiling in the range of temperatures from about 160° C. to about 390° C., a light fraction boiling below a temperature of about 160° C., and a heavy fraction boiling above a temperature of about 390° C.

42. The process of claim 41, wherein the distillate-range hydrocarbons are in the diesel fuel range.

43. The process of claim 41, wherein the light fraction contains hydrocarbons in the gasoline fuel range.

44. A process for conversion of feedstocks to distillate-range hydrocarbons for fuels containing any desired ratio of open-chain and closed-chain hydrocarbons, the method comprising the steps of:
   oligomerizing ethylene in an ethylene-containing feedstock over a first catalyst at a temperature selected between about 40° C. and about 220° C. to form a water-free first oligomerization product containing a majority concentration of mixed olefins with a carbon number between about C4 and about C8;
   oligomerizing the mixed olefins in the water-free first oligomerization product over a second catalyst at a temperature between about 150° C. and about 350° C. to form a second oligomerization product containing mixed open-chain linear and branched olefins with a carbon number between about C8 and about C23 at a yield greater than or equal to about 20%;
   optionally fractionating the second oligomerization product to obtain individual fractions, a fraction containing distillate-range olefins boiling at or higher than the fractionation temperature and a light fraction boiling at or below the fractionation temperature;
   converting ethanol in an ethanol-containing feedstock over an acid catalyst to form a first conversion product containing a majority concentration of closed-chain mixed aromatic hydrocarbons and cycloparaffin hydrocarbons with a carbon number between about C3 and about C12;
   optionally alkylating the first conversion product to produce a second conversion product comprising a selected quantity of alkylated aromatic hydrocarbons therein; and
   combining selected portions of the first conversion product, the second conversion product, and the second oligomerization product together to form a blend containing open-chain and closed-chain hydrocarbons that when hydrotreated yields a majority of fuel range hydrocarbons boiling in the range of temperatures from about 120° C. to about 390° C.

45. A process for conversion of feedstocks to distillate-range hydrocarbon fuels, comprising combining together selected portions of (a) a two-step oligomerization product and a first hydrocarbon product or (b) the two-step oligomerization product, the first hydrocarbon product, and a second hydrocarbon product to form a blend comprising any selected ratio of open-chain and closed-chain hydrocarbons, wherein:
   the first hydrocarbon product is produced by converting ethanol from an ethanol-containing feed into the first hydrocarbon product, which comprises a majority concentration of mixed cycloparaffin hydrocarbons and mixed closed-chain aromatic hydrocarbons with a carbon number between about C3 to about C12;
   the second hydrocarbon product comprises a selected quantity of alkylated aromatic hydrocarbons;
   the two-step oligomerization product is formed by
   oligomerizing an ethylene-containing feed over a first catalyst at a temperature selected from about 40° C. to about 220° C. to form a water-free first oligomerization product in a first reaction stage, wherein the water-free first oligomerization product contains a majority concentration of mixed olefins with a carbon number from about C4 to about C8; and
   oligomerizing the mixed olefins in the water-free first oligomerization product over a second catalyst at a temperature from about 150° C. to about 350° C. to form the two-step oligomerization product at a yield greater than or equal to about 20% containing mixed open-chain linear and branched olefins with a carbon number from about C8 to about C23.

* * * * *